US007265266B2

(12) United States Patent
Zhu et al.

(10) Patent No.: US 7,265,266 B2
(45) Date of Patent: Sep. 4, 2007

(54) **TRANSGENIC EVALUATION OF ACTIVATED MUTANT ALLELES OF SOS2 REVEALS A CRITICAL REQUIREMENT FOR ITS KINASE ACTIVITY AND C-TERMINAL REGULATORY DOMAIN FOR SALT TOLERANCE IN *ARABIDOPSIS THALIANA***

(75) Inventors: Jian-Kang Zhu, Riverside, CA (US); Francisco Javier Quintero-Toscano, Sevilla (ES); Jose Manuel Pardo-Prieto, Sevilla (ES); Quansheng Qiu, Urbana, IL (US); Karen Sue Schumaker, Tucson, AZ (US); Masaru Ohta, Tsukuba (JP); Changqing Zhang, Tucson, AZ (US); Yan Guo, Beijing (CN)

(73) Assignees: Arizona Board of Regents/Behalf of University of Arizona, Tucson, AZ (US); Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 11/040,005

(22) Filed: Jan. 24, 2005

(65) Prior Publication Data

US 2006/0168698 A1 Jul. 27, 2006

(51) Int. Cl.
C12N 15/82 (2006.01)
C12N 15/54 (2006.01)
C12N 15/29 (2006.01)
A01H 5/00 (2006.01)

(52) U.S. Cl. .................. 800/289; 800/312; 800/278; 800/306; 800/287; 435/419; 435/468; 435/320.1; 435/194; 536/23.6; 536/23.2

(58) Field of Classification Search .................... None
See application file for complete search history.

(56) References Cited

U.S. PATENT DOCUMENTS 6,727,408 B2   4/2004   Zhu et al.
6,784,343 B2   8/2004   Zhu et al.

OTHER PUBLICATIONS

Gong et al 2004 Plant Physiology 134:919-926.*
S.B. Gelvin, "Agrobacterium and Plant Genes Involved in T-DNA Transfer and Integration", Annu. Rev. Plant Physiol. Plant Mol. Biol., 2000, 51, pp. 223-256.
M.P. Apse, et al., "Salt Tolerance Conferred by Overexpression of a Vacuolar NA+/H+ Antiport in *Arabidopsis*", Science, vol. 285, Aug. 20, 1999, pp. 1256-1258.
A. Aronheim, et al., "Isolation of an AP-1 Repressor by a Novel Method for Detecting Protein—Protein Interactions", Molecular and Cellular Biology, vol. 17, No. 6, Jun. 1997, pp. 3094-3102.

E. Epstein, et al., "Saline Culture of Crops: a Genetic Approach", Science, New Series, vol. 210, No. 4468, Oct. 24, 1980, pp. 399-404.
R.A. Gaxiola, et al., "Drought- and Salt-Tolerant Plants Result From Overexpression of the AVP1 H+-Pump", PNAS, vol. 98, No. 20, Sep. 25, 2001, pp. 11444-11449.
S.J. Gilmour, et al., "Overexpression of the *Arabidopsis* CBF3 Transcriptional Activator MIMCS Multiple Biochemical Changes Associated With Cold Acclimation", Plant Physiology, vol. 124, Dec. 2000, pp. 1854-1865.
D. Gong, et al., "Biochemical Characterization of the *Arabidopsis* Protein Kinase SOS2 That Functions in Salt Tolerance", Plant Physiology, vol. 130, Sep. 2002, pp. 256-264.
Y. Guo, et al., Molecular Characterization of Functional Domains in the Protein Kinase SOS2 That is Required for Plant Salt Tolerance, The Plant Cell, vol. 13, Jun. 2001, pp. 1383-1399.
U. Halfter, et al., "The *Arabidopsis* SOS2 Protein Kinase Physically Interacts With and is Activated by the Calcium-Binding Protein SOS3", PNAS, vol. 97, No. 7, Mar. 28, 2000, pp. 3735-3740.
M. Ishitani, et al., "SOS3 Function in Plant Salt Tolerance Requires N-Myristoylation and Calcium Binding", The Plant Cell, vol. 12, Sep. 2000, pp. 1667-1677.
K.R. Jaglo-Ottosen, et al., "*Arabidopsis* CBF1 Overexpression Induces COR Genes and Enhances Freezing Tolerance", Science, vol. 280, Apr. 3, 1998, pp. 104-106.
H. Knight, et al., "Calcium Signalling in *Arabidopsis thaliana* responding to Drought and Salinity", The Plant Journal, 12 (5), 1997, pp. 1067-1078.
Y. Kovtun, et al., "Functional Analysis of Oxidative Stress-Activated Mitogen-Activated Protein Kinase Cascade in Plants", PNAS, vol. 97, No. 6, Mar. 14, 2000, pp. 2940-2945.
J. Liu, et al., "The *Arabidopsis thaliana* SOS2 Gene Encodes a Protein Kinase That is Required for Salt Tolerance", PNAS, vol. 97, No. 7, Mar. 28, 2000, pp. 3730-3734.
J.R. Murguia, et al. "A Salt-Sensitive 3'(2')5'-Bisphosphate Nucleotidase Involved in Sulfate Activation", Science, New Series, vol. 267, No. 5195, Jan. 13, 1995, pp. 232-234.
M. Ohta, et al., A Novel Domain in the Protein Kinase SOS2 Mediates Interaction With the Protein Phosphatase 2C AB12, PNAS, vol. 100, No. 20, Sep. 30, 2003, pp. 11771-11776.
Q.-S. Qiu, et al., "The Influence of Extracellular-Side CA2+ on the Activity of the Plasma Membrane H+-ATPASE From Wheat Roots", Aust. J. Plant Physiol., 25, 1998, pp. 923-928.

(Continued)

Primary Examiner—David T. Fox
Assistant Examiner—Brent T Page
(74) Attorney, Agent, or Firm—Oblon, Spivak, McClelland, Maier & Neustadt, P.C.

(57) ABSTRACT

The present invention provides a method of increasing salt tolerance in a plant by overexpressing a gene encoding a mutant SOS2 protein in at least one cell type in the plant. The present invention also provides for transgenic plants expressing the mutant SOS2 proteins.

40 Claims, 12 Drawing Sheets

OTHER PUBLICATIONS

Q.-S. Qiu, et al., "Regulation of SOS1, a Plasma Membrane NA+/H+ Exchanger in *Arabidopsis thaliana*, by SOS2 and SOS3", PNAS, vol. 99, No. 12, Jun. 11, 2002, pp. 8436-8441.

Q.-S. Qiu, et al., "Regulation of Vacuolar NA+/H+ Exchange in *Arabidopsis thaliana* by the Salt-Overly-Sensitive (SOS) Pathway", The Journal of Biological Chemistry, vol. 279, No. 1, Jan. 2, 2004, pp. 207-215.

F.J. Quintero, et al., "Reconstitution in Yeast of the *Arabidopsis* SOS Signaling Pathway for NA+ Homeostasis", PNAS, vol. 99, No. 13, Jun. 25, 2002, pp. 9061-9066.

A. Rus, et al., "ATHKT1 Facilitates NA+ Homeostasis and K+ Nutrition in Planta", Plant Physiology, vol. 136, Sep. 2004, pp. 2500-2511.

A. Rus, et al., "ATHKT1 is a Salt Tolerance Determinant That Controls NA+ Entry into Plant Roots", PNAS, vol. 98, No. 24, Nov. 20, 2001, pp. 14150-14155.

H. Shi, et al., "Overexpression of a Plasma Membrane NA+/H+ Antiporter Gene Improves Salt Tolerance in *Arabidopsis thaliana*", Nature Biology, vol. 21, Jan. 2003, pp. 81-85.

S-J. Wu, et al., "SOS1, a Genetic Locus Essential for Salt Tolerance and Potassium Acquisition", The Plant Cell, vol. 8, Apr. 1996, pp. 617-627.

H.-X. Zhang, et al., "Transgenic Salt-Tolerant Tomato Plants Accumulate Salt in Foliage but not in Fruit", Nature Biotechnology, vol. 19, Aug. 2001, pp. 765-768.

H.-X. Zhang, et al., "Engineering Salt-Tolerant Brassica Plants: Characterization of Yield and Seed Oil Quality in Transgenic Plants With Increased Vacuolar Sodium Accumulation", PNAS, vol. 98, No. 22, Oct. 23, 2001, pp. 12832-12836.

J.-K. Zhu, "Cell Signaling Under Salt, Water and Cold Stresses", Curr. Opin. Plant Biol., 4, pp. 401-406.

J.-K. Zhu, "Salt and Drought Stress Signal Transduction in Plants", Annu Rev. Plant Biol., 2002, 53, pp. 247-273.

Gong, D., et al., "The SOS3 Family of Calcium Sensors and SOS2 Family of Protein Kinases in *Arabidopsis*," Plant Physiology, vol. 134, Mar. 2004, pp. 919-926.

Guo, Y., et al., "Transgenic Evaluation of Activated Mutant Alleles of SOS2 Reveals a Critical Requirement for Its Kinase Activity and C-Terminal Regulatory Domain for Salt Tolerance in *Arabidopsis thaliana*," The Plant Cell, vol. 16, Feb. 2004, pp. 435-449.

* cited by examiner

TRANSGENIC EVALUATION OF ACTIVATED MUTANT ALLELES OF SOS2 REVEALS A CRITICAL REQUIREMENT FOR ITS KINASE ACTIVITY AND C-TERMINAL REGULATORY DOMAIN FOR SALT TOLERANCE IN *ARABIDOPSIS THALIANA*

STATEMENT REGARDING FEDERALLY FUNDED PROJECT

The United States Government owns certain rights in the present invention pursuant to funding from the National Institutes of Health Grant R01GM59138, and the U.S. Department of Energy Grant DE-FG03-93ER20120.

BACKGROUND OF THE INVENTION

1. Field of the Invention

The present invention provides a method of increasing salt tolerance in a plant by overexpressing a gene encoding a mutant SOS2 protein in at least one cell type in the plant. The present invention also provides for transgenic plants expressing the mutant SOS2 proteins.

2. Discussion of the Background

Soil salinity is a serious environmental stress limiting plant productivity. Sodium ions ($Na^+$), which are abundant in saline soils, are cytotoxic in plants when they accumulate to high concentrations. $Na^+$ enters plant cells through transporters such as HKT1 (Rus et al., 2001) and nonselective cation channels (Amtmann and Sanders, 1999). To prevent $Na^+$ buildup in the cytoplasm, plant cells employ $Na^+/H^+$ antiporters at the plasma membrane and tonoplast to transport $Na^+$ into the apoplast and vacuole, respectively (Apse et al., 1999; Qiu et al., 2002). Overexpression of the *Arabidopsis thaliana* plasma membrane $Na^+/H^+$ antiporter Salt Overly Sensitivel (SOS1) or the vacuolar $Na^+/H^+$ antiporter AtNHX1 improves salt tolerance in transgenic plants (Apse et al., 1999; Zhang and Blumwald, 2001; Zhang et al., 2001; Shi et al., 2003). Enhanced salt tolerance can also be achieved by overexpression of the vacuolar $H^+$-pyrophosphatase AVP1, which generates the driving force for $Na^+$ transport into the vacuole (Gaxiola et al., 2001).

Recently, a regulatory pathway for ion homeostasis and salt tolerance was identified in *A. thaliana* (Zhu, 2000, 2002). Salt stress is known to elicit a rapid increase in the free calcium concentration in the cytoplasm (Knight et al., 1997). SOS3, a myristoylated calcium binding protein, is proposed to sense this calcium signal (Liu and Zhu, 1998; Ishitani et al., 2000). SOS3 physically interacts with the protein kinase SOS2 and activates the substrate phosphorylation activity of SOS2 in a calcium-dependent manner (Halfter et al., 2000; Liu et al., 2000). SOS3 also recruits SOS2 to the plasma membrane, where the SOS3-SOS2 protein kinase complex phosphorylates SOS1 to stimulate its $Na^+/H^+$ antiport activity (Qiu et al., 2002; Quintero et al., 2002). Loss-of-function mutations in SOS3, SOS2, or SOS1 cause hypersensitivity to $Na^+$ (Zhu et al., 1998).

SOS2 has a highly conserved N-terminal catalytic domain similar to that of *Saccharomyces cerevisiae* SNF1 and animal AMPK (Liu et al., 2000). Within the SOS2 protein, the N-terminal catalytic region interacts with the C-terminal regulatory domain (Guo et al., 2001). SOS3 interacts with the FISL motif in the C-terminal region of SOS2 (Guo et al., 2001), which serves as an auto-inhibitory domain. A constitutively active SOS2 kinase, T/DSOS2, can be engineered by a $Thr^{168}$-to-Asp change (to mimic phosphorylation by an upstream kinase) in the putative activation loop. The kinase activity of T/DSOS2 is independent of SOS3 and calcium (Guo et al., 2001). Removing the FISL motif (SOS2DF) or the entire C-terminal regulatory domain (SOS2/308) may result in constitutively active forms of SOS2 (Guo et al., 2001; Qiu et al., 2002). The activation loop mutation and the autoinhibitory domain deletions have a synergistic effect on the kinase activity of SOS2, and superactive SOS2 kinases T/DSOS2/308 or T/DSOS2/DF can be created when the two changes are combined (Guo et al., 2001; Qiu et al., 2002). The present inventors have shown that T/DSOS2/DF could activate the transport activity of SOS1 in vitro, whereas the wild-type SOS2 protein could not (Qiu et al., 2002). However, at the time of the present invention, whether these active forms of SOS2 can function in vivo was not known.

In the trophic chain, plant roots play pivotal roles by taking up mineral nutrients from soil solutions. Plant roots experience constant fluctuations in soil environments. A frequent variant in the soil solution is $Na^+$ concentration (Epstein et al., 1980). $Na^+$ is not an essential ion for most plants. In fact, the growth of the majority of plants, e.g., glycophytes, is inhibited by the presence of high concentrations of soil $Na^+$. External $Na^+$ causes $K^+$ deficiency by inhibiting $K^+$ uptake into plant cells (Wu et al., 1996). $Na^+$ accumulation within the cell is toxic to many cytosolic enzymes. In contrast, many cellular enzymes are activated by $K^+$, which is the most abundant cation in the cytoplasm. Certain cytoplasmic enzymes are especially prone to $Na^+$ inhibition when $K^+$ concentration is reduced (Murguia et al., 1995). Therefore, maintaining intracellular $K^+$ and homeostasis to preserve a high $K^+/Na^+$ ratio is important for all cells and especially critical for plant cells.

Because of limited water supplies and the widespread use of irrigation, the soils of many cultivated areas have become increasingly salinized. In particular, modern agricultural practices such as irrigation impart increasing salt concentrations when the available irrigation water evaporates and leaves previously dissolved salts behind. As a result, the development of salt tolerant cultivars of agronomically important crops has become important in many parts of the world; for example, in salty soil found in areas such as Southern California, Arizona, New Mexico and Texas.

Dissolved salts in the soil increase the osmotic pressure of the solution in the soil and tend to decrease the rate at which water from the soil will enter the roots. If the solution in the soil becomes too saturated with dissolved salts, the water may actually be withdrawn from the plant roots. Thus the plants slowly starve though the supply of water and dissolved nutrients may be more than ample.

Salt tolerant plants can facilitate use of marginal areas for crop production, or allow a wider range of sources of irrigation water. Traditional plant breeding methods have, thus far, not yielded substantial improvements in salt tolerance and growth of crop plants. In addition, such methods require long-term selection and testing before new cultivars can be identified.

Accordingly, there is a need to improve and/or increase salt tolerance in plants, particularly those plants that are advantageously useful as agricultural crops.

SUMMARY OF THE INVENTION

In order to address the aforementioned problems in the art, the present inventors identified various activated SOS2 proteins in *S. cerevisiae* and *A. thaliana*. Further, the present inventors found that the protein kinase activity of these SOS2 proteins is sufficient for activation of the SOS1 plasma membrane $Na^+/H^+$ antiporter in vivo and in planta. Such a result enables the identification of the domains in the SOS2 protein that are important for in planta function.

Accordingly, it is an object of the present invention to provide a method of increasing salt tolerance in a plant by overexpressing a gene encoding a mutant SOS2 protein in at least one cell type in the plant.

This object may be achieved by expressing a gene encoding a mutant SOS2 protein have a sequence selected from SEQ ID NO: 4, SEQ ID NO: 6, SEQ ID NO: 8, and SEQ ID NO: 10. Alternatively, the gene may have a sequence selected from SEQ ID NO: 3, SEQ ID NO: 5, SEQ ID NO: 7, and SEQ ID NO: 9.

In another object of the present invention, the aforementioned method is performed in the presence of a vector containing a polynucleotide sequence that is at least 70% homologous to SEQ ID NO: 11, where the polynucleotide sequence encodes a protein having SOS3 calcium-binding activity. Thus, the polynucleotide sequence may be SEQ ID NO: 11 or may encode a protein of SEQ ID NO: 12.

In a preferred object of the present invention, each gene or polynucleotide sequence to be expressed is operably linked to a promoter that is functional in a plant cell, wherein the promoter regulates expression of the same.

In yet another object of the present invention is a transgenic plant harboring a vector for expressing a gene encoding a mutant SOS2 protein in at least one cell type in the plant. This object may be achieved by expressing a gene encoding a mutant SOS2 protein have a sequence selected from SEQ ID NO: 4, SEQ ID NO: 6, SEQ ID NO: 8, and SEQ ID NO: 10. Alternatively, the gene may have a sequence selected from SEQ ID NO: 3, SEQ ID NO: 5, SEQ ID NO: 7, and SEQ ID NO: 9. As in the previous object, it is preferred that each gene or polynucleotide sequence be expressed is operably linked to a promoter that is functional in a plant cell, wherein the promoter regulates expression of the same; however, the aforementioned genes for the SOS2 mutants may also be integrated into the genome of the transgenic plant.

In another object of the present invention, the aforementioned transgenic plant contains a vector containing a polynucleotide sequence that is at least 70% homologous to SEQ ID NO: 11, where the polynucleotide sequence encodes a protein having SOS3 calcium-binding activity. Thus, the polynucleotide sequence may be SEQ ID NO: 11 or may encode a protein of SEQ ID NO: 12.

Although the plants for the objects above may be any monochot or dichot, it is preferable that the plant be one of *Arabidopsis thalania*, wheat, corn, peanut cotton, oat, or soybean.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

Model of the domains of the wild-type and altered SOS2 protein kinases (A) is shown. The kinase activities (autophosphorylation and phosphorylation of an in vitro substrate) of altered forms of SOS2 (GST fusion proteins of T/DSOS2, T/DSOS2/308, T/DSOS2DF, and T/DSOS2/329) were evaluated. T/DSOS2 (polynucleotide sequence=SEQ ID NO: 3; protein sequence=SEQ ID NO: 4), T/DSOS2/308 (polynucleotide sequence=SEQ ID NO: 5; protein sequence=SEQ ID NO: 6), and T/DSOS2/329 (polynucleotide sequence=SEQ ID NO: 7; protein sequence=SEQ ID NO: 8) were obtained as described in Guo et al., 2001, while T/DSOS2DF (polynucleotide sequence=SEQ ID NO: 9; protein sequence=SEQ ID NO: 10) was obtained as described in Qiu et al, 2002. After the autophosphorylation assays, protein was separated by SDS-PAGE, and the gel was stained with Coomassie blue (B) and exposed to x-ray film (C). The ability of the same GST-SOS2 fusion proteins to phosphorylate the peptide substrate p3 (400 pmol per assay) was determined (D).

Figure 2:
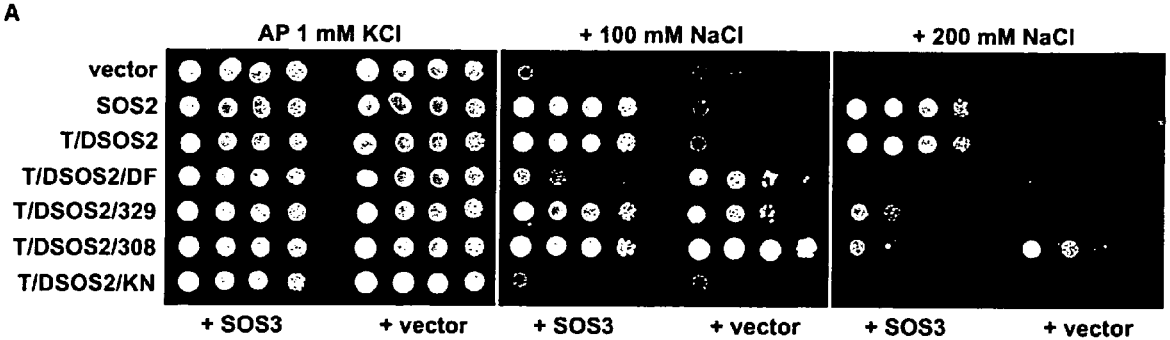
Figure 2:
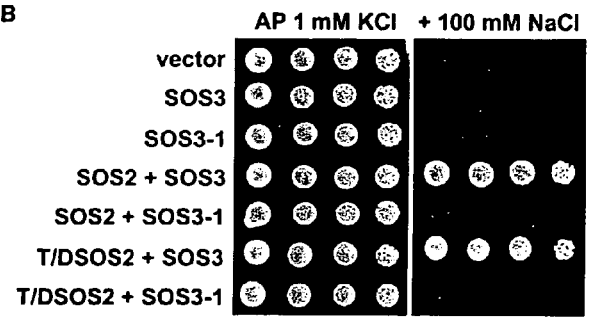
Figure 2:
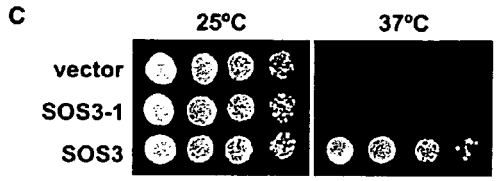

FIG. 2: Competence of Various Forms of the SOS2 Kinase and the Ancillary Protein SOS3 to Increase the Salt Tolerance of *S. cerevisiae* Expressing SOS1.

(A) Wild-type SOS2, activated SOS2 kinases (T/DSOS2, T/DSOS2/DF, T/DSOS2/329, and T/DSOS2/308), and inactive SOS2 mutant (T/DSOS2/KN) were cotransformed with or without SOS3 into *S. cerevisiae* strain YP890 cells. Transformants were grown overnight in liquid AP medium with 1 mM KCl, and 5 µL of serial decimal dilutions were spotted onto plates containing AP medium with 1 mM KCl or supplemented with 100 or 200 mM NaCl. Plates were incubated at 28° C. and photographed after 4 d.

(B) Wild-type SOS2 and activated kinase T/DSOS2 were coexpressed with wild-type SOS3 or mutant SOS3-1 in YP890 cells. Salt tolerance that resulted from the combination of these proteins was determined as indicated above.

(C) Cdc25-2 cells carrying plasmid pSRS2-1 for the expression of an hSos:SOS2 chimera were transformed to produce wild-type SOS3 or mutant SOS3-1 proteins, or with an empty vector. Cells were grown overnight at 25° C. in selective medium and then spotted on duplicate YPD plates that were incubated for 2 d at either 25° C. or 37° C. Growth at 37° C. indicates targeting of the SOS2 kinase to the plasma membrane.

Figure 3:
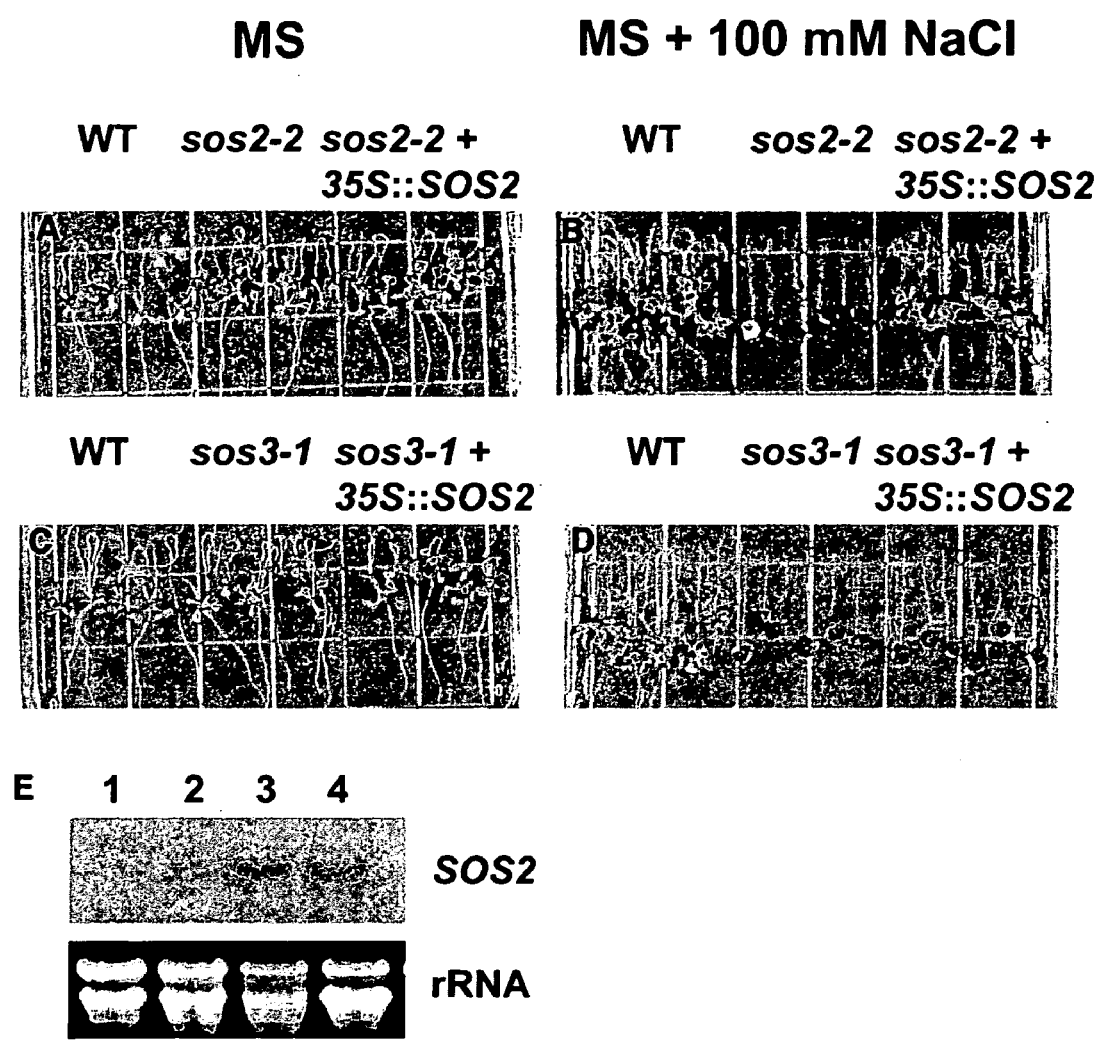

FIG. 3: Expression of SOS2 Complements the sos2-2 Salt-Sensitive Phenotype but Not the sos3-1 Salt-Sensitive Phenotype.

Five-day-old seedlings grown on MS agar medium were transferred to MS agar medium without NaCl ([A] and [C]) or with 100 mM NaCl ([B] and [D]); photographs were taken 10 d after transfer. SOS2 transcript levels in sos2-2, sos3-1, and 35S:SOS2 transgenic lines (E) are shown. RNA gel blot analysis was performed with total RNA extracted from sos2-2 (1), sos3-1 (2), sos2-2 (3), and sos3-1 (4) transgenic plants grown in the absence of NaCl. 25S rRNA (ethidium bromide stained) was used as a loading control. WT, wild type.

Figure 4:
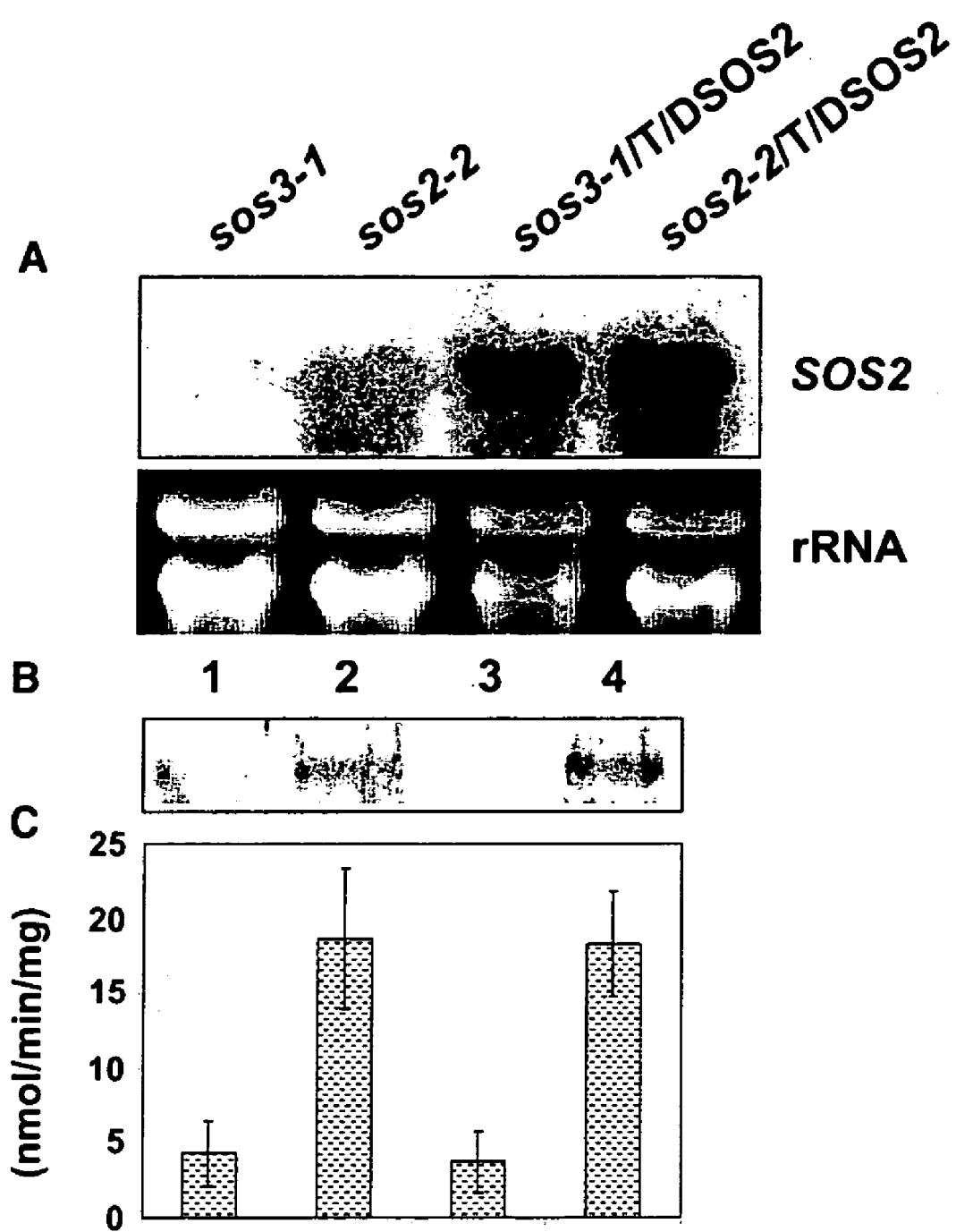

FIG. 4: Expression of T/DSOS2 in sos2-2 and sos3-1.

RNA gel blot analysis of T/DSOS2 expression in sos3-1, sos2-2 or sos3-1 and sos2-2 transgenic lines grown in the absence of NaCl (A). 25S rRNA (ethidium bromide stained) was used as a loading control. Total protein was extracted from mutant and transgenic plants and incubated with GST-SOS3 coupled to glutathione-Sepharose beads. The GST-SOS3-T/DSOS2/SOS2 complex was used for immunoblot analysis (B) with protein from sos3-1 (1) and sos2-2 (3) mutants or sos3-1 (2) and sos2-2 (4) transgenic lines. Proteins were probed with anti-SOS2 antibody. The GST-SOS3-T/DSOS2/SOS2 complex was also used for peptide phosphorylation assays (C) with protein from sos3-1 (1), the sos3-1 transgenic line (2), sos2-2 (3), and the sos2-2 transgenic line (4).

Figure 5:
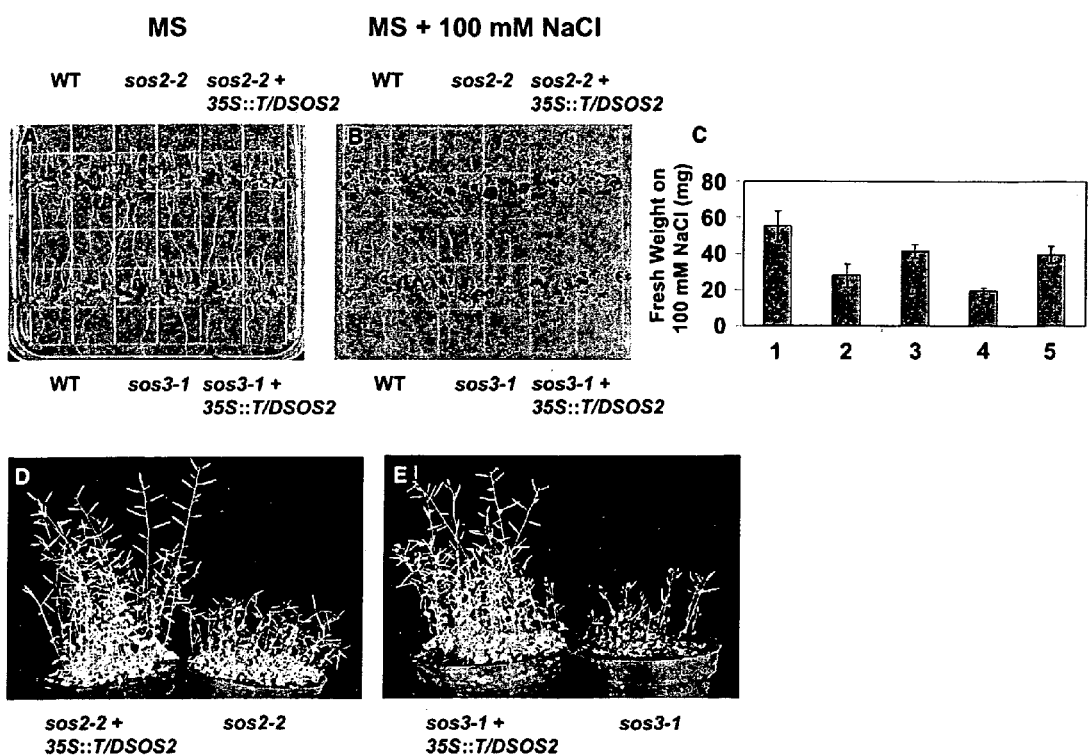

FIG. 5: Expression of T/DSOS2 Partially Rescues the sos2-2 and sos3-1 Salt-Hypersensitive Phenotypes.

Five-day-old seedlings grown on MS agar medium were transferred to MS agar medium without NaCl (A) or with 100 mM NaCl (B); photographs were taken 10 d after transfer. Fresh weight (C) (in milligrams) of five plants of the wild type (1), sos3-1 (2), sos3-1 transgenic line (3), sos2-2 (4), and sos2-2 transgenic line (5) 2 weeks after transfer to MS+100 mM NaCl (mean±SE of three replicate experiments). Growth of sos2-2 and a sos2-2 transgenic line (D) and sos3-1 and a sos3-1 transgenic line (E) in soil in which the NaCl levels were increased by 50 mM every 4 d until a final concentration of 200 mM was reached. Photographs were taken after 15 d in 200 mM NaCl.

Figure 6:
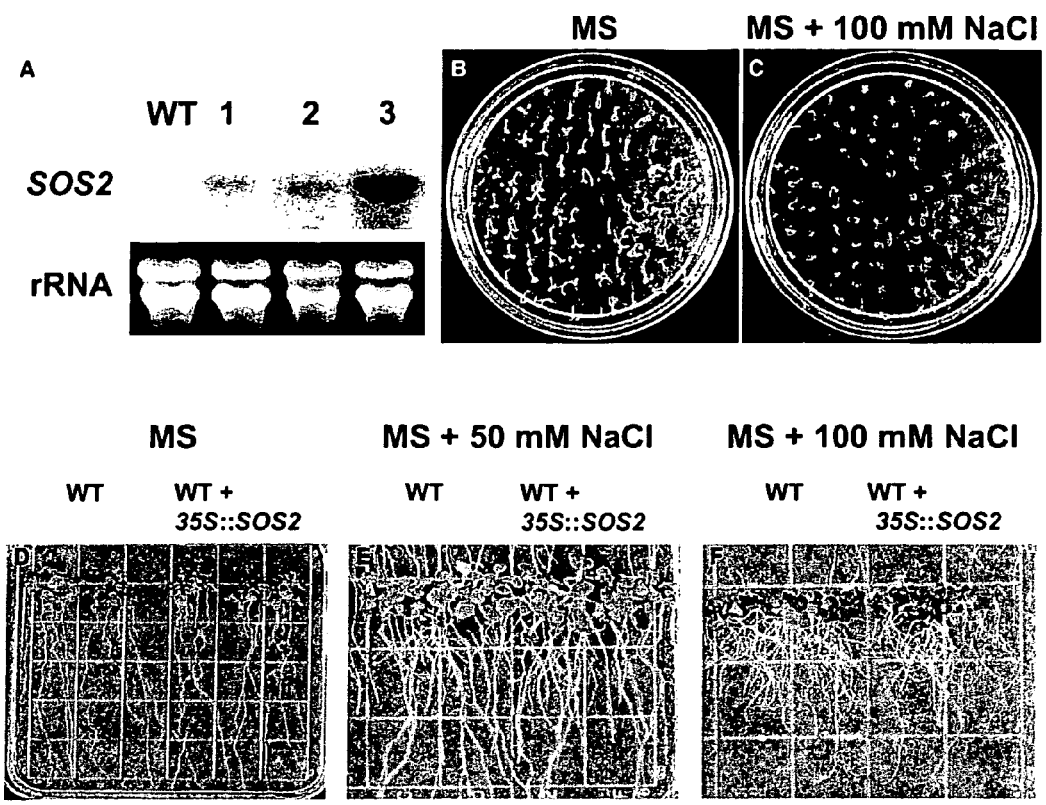

FIG. 6: Expression of SOS2 Does Not Increase Salt Tolerance in *A. thaliana*.

SOS2 transcript levels in the wild type and three 35S: SOS2 transgenic lines grown in the absence of NaCl (A) are shown. 25S rRNA (ethidium bromide stained) was used as a loading control. Seeds from the wild type (top) and two 35S:SOS2 transgenic lines (bottom) were germinated on MS medium (B) or MS+100 mM NaCl (C); photographs were taken 5 (left panel) and 10 d (right panel) after germination. Five-day-old seedlings grown on MS agar medium were transferred to MS agar without NaCl (D) or with 50 (E) or 100 mM NaCl (F); photographs were taken 10 d after transfer.

Figure 7:
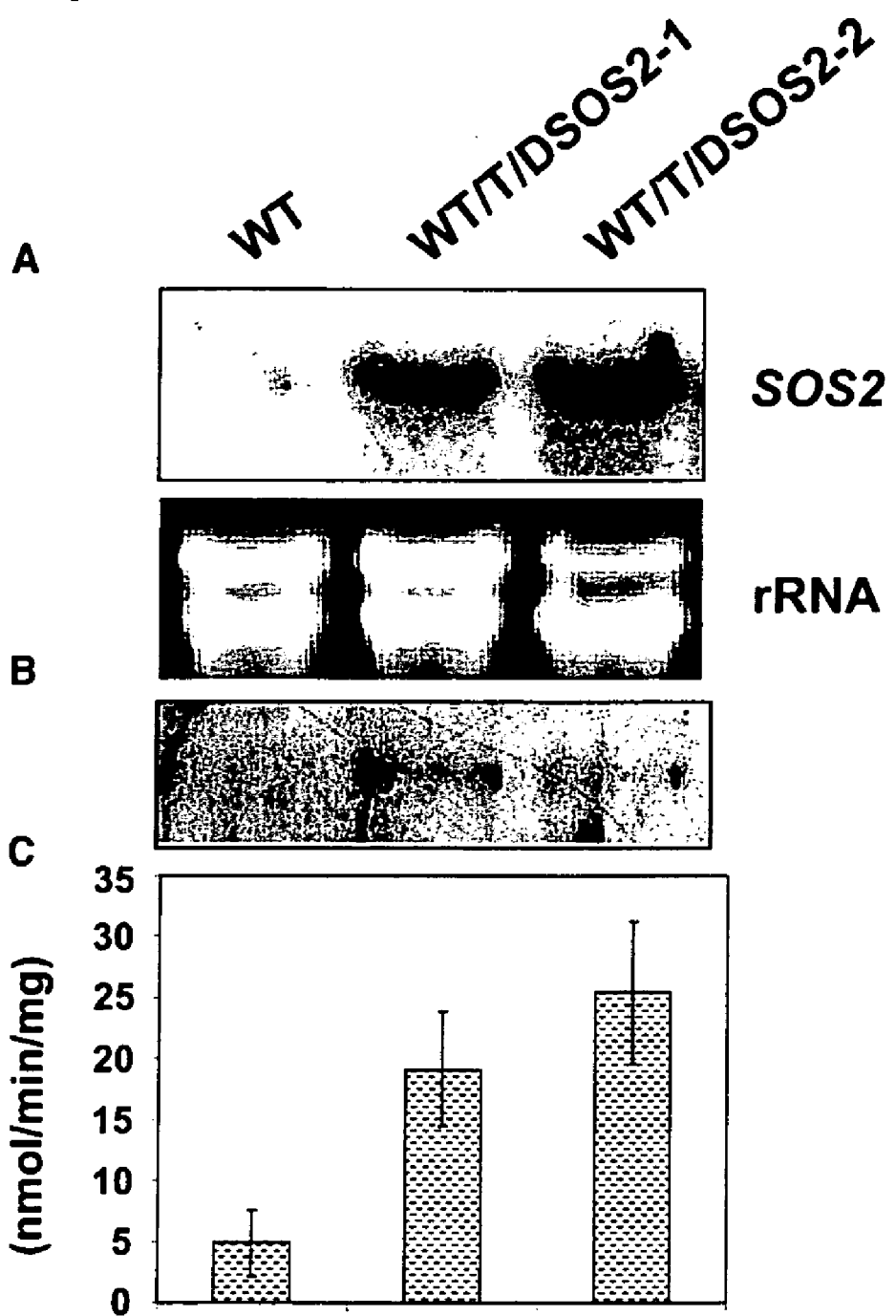

FIG. 7: Expression of T/DSOS2 in *A. thaliana*.

T/DSOS2 transcript levels in the wild-type and WT/T/DSOS2 transgenic lines (A). RNA gel blot analysis with total RNA extracted from the wild type and two WT/T/DSOS2 lines grown in the absence of NaCl. 25S rRNA (ethidium bromide stained) was used as a loading control. Total protein was extracted from the wild-type and transgenic plants and incubated with GST-SOS3 coupled to glutathione-Sepharose beads. The GST-SOS3-T/DSOS2/SOS2 protein complex was used for immunoblot analysis with anti-SOS2 antibody (B) and peptide phosphorylation assays (C).

Figure 8:
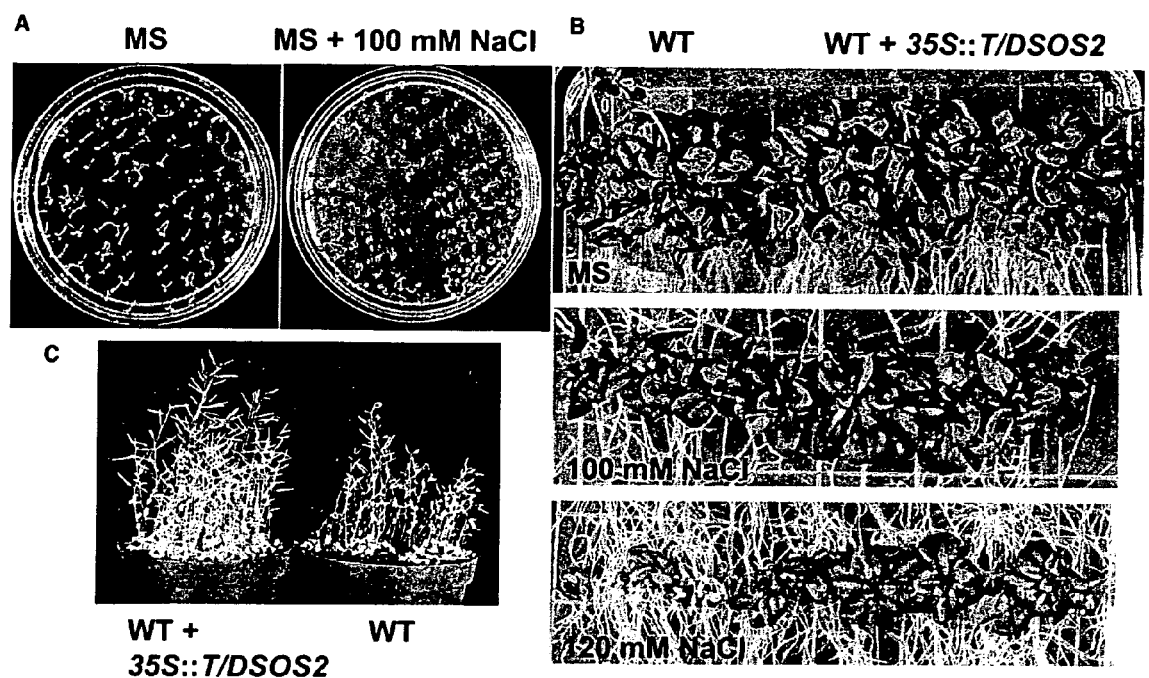

FIG. 8: Expression of T/DSOS2 Increases Salt Tolerance in *A. thaliana*.

(A) Seeds from the wild type (top) and two WT/T/DSOS2 transgenic lines (bottom) were germinated on MS medium (left panel) or MS+100 mM NaCl (right panel); photographs were taken 5 (left panel) and 10 d (right panel) after germination.

(B) Five-day-old seedlings from the wild type or WT/T/DSOS2 transgenic lines grown on MS agar were transferred to MS agar without NaCl (top panel), with 100 (middle panel), or 120 mM NaCl (bottom panel); photographs were taken 15 d after transfer.

(C) Wild-type and transgenic (WT+35S:T/DSOS2) plants were grown in soil in which the NaCl levels were increased by 50 mM every 4 d until a final concentration of 200 mM was reached. Photographs were taken after 15 d in 200 mM NaCl.

Figure 9:
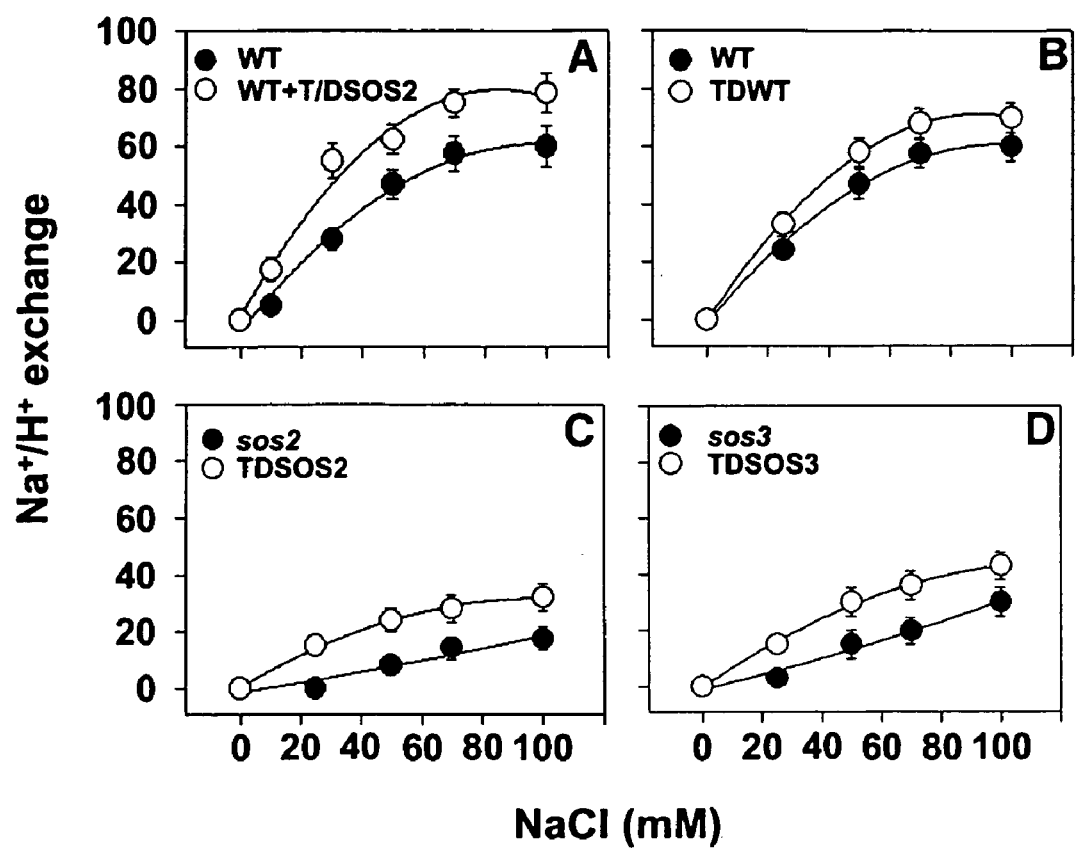

FIG. 9: Active T/DSOS2 Increases Plasma Membrane $Na^+/H^+$-Exchange Activity in Vitro and in Vivo.

When added in vitro, T/DSOS2 protein stimulates plasma membrane $Na^+/H^+$-exchange (antiport) activity in vesicles isolated from wild-type plants (A). Transport assays were performed as described in Methods. The pH gradient ($\Delta$pH) was formed in the absence (closed circle) or presence (open circle) of T/DSOS2 protein. When $\Delta$pH reached steady state, NaCl was added over a range of final concentrations (0 to 100 mM), and the initial rates of dissipation ($Na^+/H^+$ exchange) were measured. When compared with activity in the wild type, sos2, and sos3, plasma membrane $Na^+/H^+$-exchange activity is higher in the wild-type (B), sos2 (C), and sos3 (D) plants overexpressing T/DSOS2. Assays were performed using vesicles isolated from the parental (closed circle, [B] to [D]) and transgenic (open circle, [B] to [D]) plants. When $\Delta$pH reached steady state, NaCl was added over a range of final concentrations (0 to 100 mM), and the initial rates of dissipation were measured. Units of $Na^+/H^+$ exchange are $\Delta$%F $mg^{-1}$ protein $min^{-1}$. Data in (A) to (D) represent mean±SE of at least three replicate experiments. Each replicate experiment was performed using independent membrane preparations.

Figure 10:
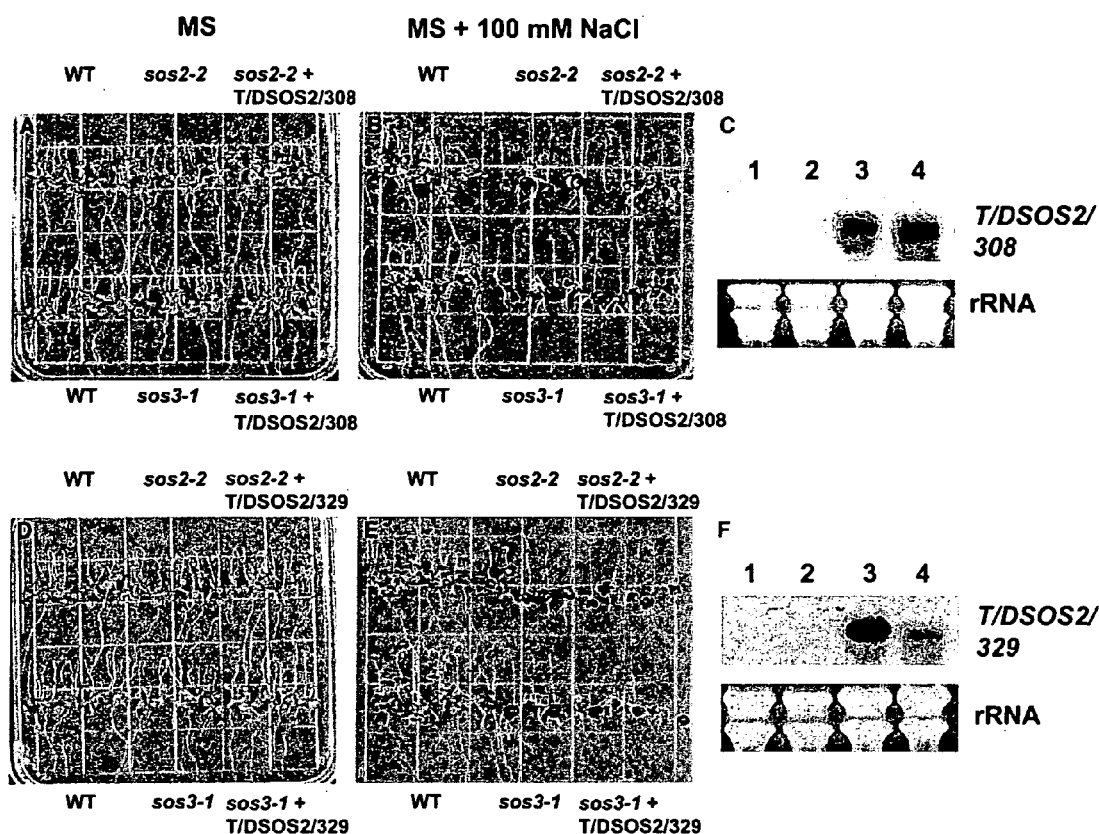

FIG. 10: Expression of T/DSOS2/308 or T/DSOS2/329 Does Not Complement the sos2-2 and sos3-1 Salt-Sensitive Phenotypes.

Five-day-old seedlings grown on MS agar medium were transferred to MS agar medium without NaCl ([A] and [D]) or with 100 mM NaCl ([B] and [E]); photographs were taken 10 d after transfer. T/DSOS2/308 (C) or T/DSOS2/329 (F) transcript levels in sos2-2 (1), sos3-1 (2), or sos2-2 (3) and sos3-1 (4) transgenic lines grown in the absence of NaCl. 25S rRNA (Ethidium bromide stained) was used as a loading control.

Figure 11:
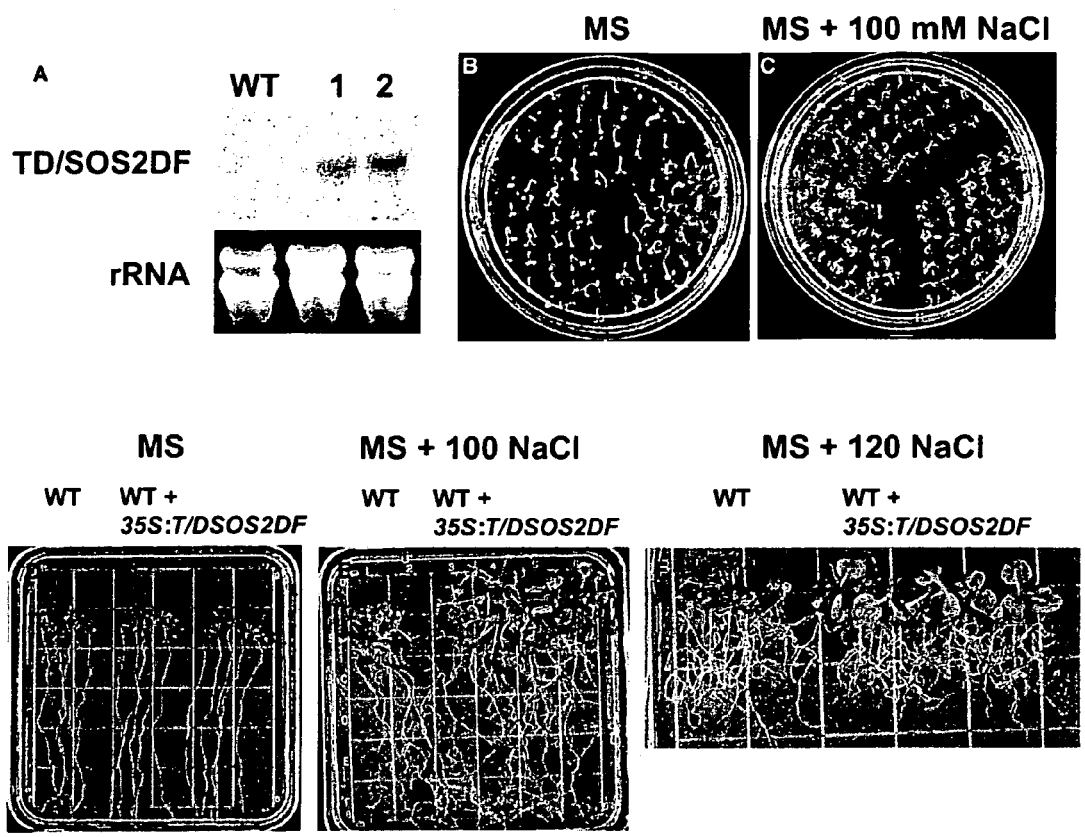

FIG. 11: Expression of T/DSOS2DF Increases Salt Tolerance in *A. thaliana*.

T/DSOS2DF transcript levels in the wild type and two transgenic lines grown in the absence of NaCl (A). 25S rRNA (ethidium bromide stained) was used as a loading control. Seeds from the wild type (top) and two transgenic lines (bottom) were germinated on MS medium (B) or MS+100 mM NaCl (C); photographs were taken 5 (left panel) and 10 d (right panel) after germination. Five-day-old seedlings grown on MS agar medium were transferred to MS agar without NaCl (D) or with 100 (E) or 120 mM NaCl (F); photographs were taken 10 (D) and 15 d ([E] and [F]) after transfer.

Figure 12:
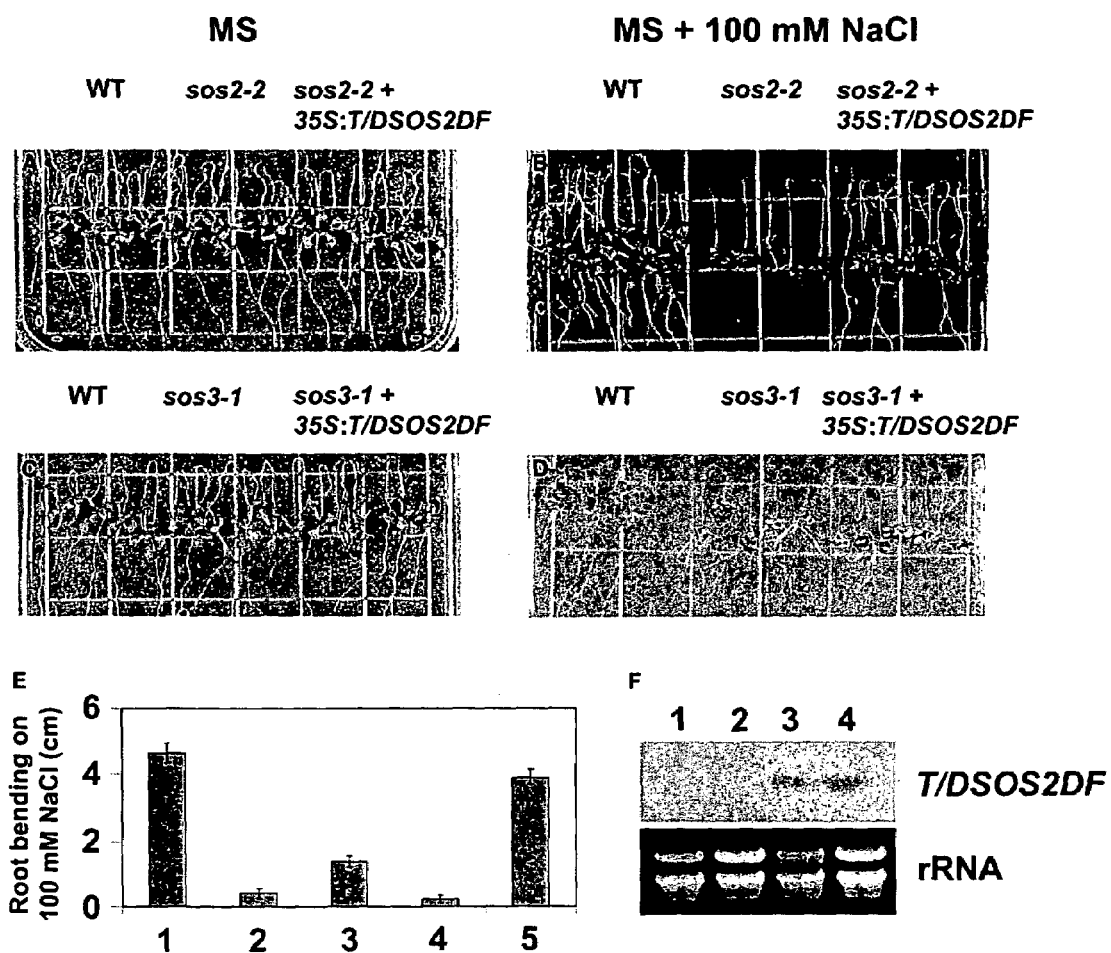

FIG. 12: Expression of T/DSOS2DF Rescues the sos2-2 Salt-Hypersensitive Phenotype but Not the sos3-1 Salt-Hypersensitive Phenotype.

Five-day-old seedlings grown on MS agar medium were transferred to MS agar medium without NaCl ([A] and [C]) or with 100 mM NaCl ([B] and [D]); photographs were taken 10 d after transfer. Root growth (E) (in centimeters) of the wild type (1), sos3-1 (2), a sos3-1 transgenic line (3), sos2-2 (4), and a sos2-2 transgenic line (5) grown on MS medium transcript levels (F) are shown. RNA gel blot analysis with total RNA extracted from sos2-2 (1), sos3-1 (2), a sos2-2 transgenic line (3), and a sos3-1 transgenic line (4) grown in the absence of NaCl. 25S rRNA (ethidium bromide stained) was used as a loading control.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, plant biology, and the medical sciences.

All methods and materials similar or equivalent to those described herein can be used in the practice or testing of the present invention, with suitable methods and materials being described herein. All patents, patent applications, publications, and other references mentioned herein are incorporated by reference in their entirety. In case of conflict, the present specification, including definitions, will control. Further, the materials, methods, and examples are illustrative only and are not intended to be limiting, unless otherwise specified.

Genetic analysis of sos1, sos2, and sos3 mutants suggested that SOS1, SOS2, and SOS3 function in the same pathway for Na$^+$ homeostasis in *A. thaliana* (Zhu et al., 1998). SOS2 is activated by its interaction with the SOS3 protein in a calcium-dependent manner (Halfter et al., 2000). When expressed in *S. cerevisiae*, the SOS3-SOS2 complex phosphorylates and activates SOS1 to enhance Na$^+$ efflux and salt tolerance (Quintero et al., 2002). The Na$^+$/H$^+$ exchange activity of SOS1 is substantially diminished in sos2 and sos3 mutant plants, and in vitro addition of the activated form of SOS2, T/DSOS2DF, rescues the exchange activity in not only sos2 but also sos3 plasma membrane vesicles (Qiu et al., 2002). Therefore, the requirement of SOS3 in vitro for SOS1 activation can be by-passed by pre-forming the activated SOS2 protein.

Results presented herein demonstrate that in *S. cerevisiae*, the requirement of SOS3 in salt tolerance can also be partially by-passed in vivo by the activated forms of SOS2. However in planta, only the activated form of SOS2 that retains structural integrity (i.e., T/DSOS2) can by-pass the requirement for SOS3. These results show that data obtained in vitro, and even in vivo, from a heterologous system only partially reflect what happens in planta. The in planta experiments thus reveal new functions of the regulatory proteins and their essential structural domains.

The activity and functionality of the different forms of SOS2 in vitro, in *S. cerevisiae*, and in wild-type and mutant *A. thaliana* is summarized in Table 1 (infra). In *S. cerevisiae*, the effect of the kinase forms on SOS1 activation and salt tolerance is largely correlated with their in vitro kinase activities when both are measured in the absence of SOS3.

For example, T/DSOS2/308 is most active in vitro and is also most effective in enhancing the salt tolerance of the *S. cerevisiae* cells not expressing SOS3, whereas wild-type SOS2 is essentially inactive in both assays. By contrast, the ability of SOS2 variants to activate SOS1 in vivo is also dependent on their ability to interact with the ancillary protein SOS3 through the FISL motif. Thus, activated forms T/DSOS2 and T/DSOS2/329, both containing the FISL motif, conveyed greater salt tolerance in the presence of SOS3, whereas T/DSOS2DF and T/DSOS2/308 did not.

The results demonstrate that localization of activated SOS2 to the membrane via its interaction with SOS3 enhances but is not necessary for activation of SOS1. Structural integrity of SOS2 is also important because SOS2-SOS3 and T/DSOS2-SOS3 complexes yielded maximal activation of SOS1 and salt tolerance above 100 mM NaCl (FIG. 2 and data not shown).

Although T/DSOS2/308, T/DSOS2/DF, and T/DSOS2/329 are all more active in vitro and result in limited independence from SOS3 in *S. cerevisiae* cells, they are unable to bypass the SOS3 deficiency in planta. Surprisingly, only the T/DSOS2 form was able to partially rescue the sos3-1 mutant phenotype when expressed in *A. thaliana*, despite the strict dependence of T/DSOS2 on a functional SOS3 protein in *S. cerevisiae*. The sos3-1 mutation causes a deletion of three amino acids in one of the EF hands of SOS3 that reduces but does not eliminate the calcium binding of SOS3 (Liu and Zhu, 1998; Ishitani et al., 2000). It is therefore possible that this mutant form of SOS3 is still partially functional. Because T/DSOS2DF, which varies from T/DSOS2 only in the removal of the FISL motif, did not suppress the sos3-1 mutation whereas T/DSOS2 did, it was possible that the mutant polypeptide SOS3-1 could still bind to T/DSOS2 and target the activated kinase to the plasma membrane for the phosphorylation of SOS1. However, previous studies have shown that the mutant SOS3-1 protein does not interact with SOS2 in an *S. cerevisiae* two-hybrid assay (Ishitani et al., 2000), and the present inventors show herein that SOS3-1 is unable to recruit SOS2 or T/DSOS2 to the plasma membrane (FIGS. 2B and 2C).

Alternatively, T/DSOS2 could interact with another SOS3-like calcium binding protein (SCaBP) and be targeted to the plasma membrane in the absence of SOS3. If so, it would also explain why T/DSOS2DF partially rescued the sos2-2 mutant phenotype but could not suppress the sos3-1 mutation because deletion of the FISL motif eliminates interaction with SOS3 and other SCaBPs. The sos2-2 mutation results in a truncated protein containing the kinase catalytic domain (Liu et al., 2000). It cannot be ruled out that the truncated protein in the mutant may influence the results in planta. It should also be noted that SOS2 physically interacts with other proteins that, directly or indirectly, may help recruit T/DSOS2 to membranes in a SOS3-independent manner. For instance, it has been recently shown that SOS2 binds to ABI2, a protein phosphatase 2C involved in abscisic acid and stress signaling (Ohta et al., 2003. Moreover, it is reasonable to expect that SOS2, besides activating SOS1, may fulfill additional roles leading to plant salt tolerance that could be independent of its interaction with SCaBPs and/or targeting to the plasma membrane. The discoveries here collectively reveal a requirement for the C-terminal regulatory region of SOS2 for salt tolerance in planta.

Another unexpected discovery is that T/DSOS2 partially rescues the salt hypersensitivity in the shoot but not the root in sos2 and sos3 mutants. The lack of effect in the root is not likely explained by the use of the CaMV 35S promoter because the wild-type SOS2 expressed under the same promoter does rescue the sos2 mutant in both the shoot and root. A root-specific regulation of SOS2 may occur through its activation loop, and the T/D mutation may interfere with such a regulation. Although the hypothetical upstream protein kinase(s) for SOS2 has not been identified, it is conceivable that there might be a root-specific isoform of such a kinase. On the other hand, expression of T/DSOS2DF can rescue the sos2 mutant phenotype. Thus, if the hypothetical root-specific upstream kinase is responsible for the inactivity of T/DSOS2 in the root, it must not have an effect on T/DSOS2DF.

Regulatory genes are often considered superior targets of biotechnological applications for plant improvement because they control many downstream effector genes. For example, ectopic expression of the CBF/DREB1A family of transcription factors and the MAPKKK ANP1 have been shown to substantially improve plant tolerance to various abiotic stresses (Jaglo-Ottosen et al., 1998; Gilmour et al., 2000; Kovtun et al., 2000). SOS2 is a key regulator of ion transporters (Zhu, 2002), some of which have been shown to confer increased salt tolerance when overexpressed in transgenic plants (Apse et al., 1999; Shi et al., 2003). In 10 this study, the present inventors evaluated the feasibility of using SOS2 to improve plant salt tolerance. Overexpression of the wild-type SOS2 did not confer any increased salt tolerance in transgenic *A. thaliana*. However, ectopic expression of the activated forms T/DSOS2 and T/DSOS2/DF led to measurable enhancement in salt tolerance in transgenic *A. thaliana*. These results raise the hope that by exploring various versions of the protein kinase, an effective allele may be identified that might become useful even in field conditions.

Accordingly, the present invention is embodied by the description provided herein and further explained and exemplified below.

The term "plant" includes whole plants, plant organs (e.g., leaves, stems, roots, etc.), seeds and plant cells and progeny of same. The class of plants, which can be used in the methods of the invention, is generally as broad as the class of higher plants amenable to transformation techniques, including both monocotyledonous and dicotyledonous plants. Preferred plants include rice, corn, wheat, cotton, peanut, and soybean.

Thus, in one embodiment of the present invention, salt tolerance can be enhanced or increased by increasing the amount of protein available in the plant, preferably by the enhancement of the sos2 mutant genes in the plant.

Thus, one embodiment of the present invention is plant cells carrying the polynucleotides encoding the sos2 mutants of the present invention, and preferably transgenic plants carrying the isolated polynucleotide.

As used herein, the term "enhancement" means increasing the intracellular activity of one or more enzymes in a plant cell and/or plant, which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene may act in the same manner. In addition, it is possible to increase expression by employing inducible promoters. A gene can also be used which encodes a corresponding enzyme with a high activity. Expression can also be improved by measures for extending the life of the mRNA. Furthermore, preventing the degradation of the enzyme increases enzyme activity as a whole. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

An "expression cassette" as used herein includes a promoter, which is functional in a plant cell, operably linked to a nucleic acid encoding a SOS2 mutant in accordance with the present invention as represented by SEQ ID NOs: 4, 6, 8, and 10 (e.g., a polynucleotide having the sequence of SEQ ID NOs: 3, 5, 7, and 9, respectively), wherein enhanced expression of the protein in a plant cell imparts increased salt tolerance to said plant cell.

In a preferred embodiment of the present invention the promoter is selected from the group consisting of a viral coat protein promoter, a tissue-specific promoter, a monocot promoter, a ubiquitin promoter, a stress inducible promoter, a CaMV 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Ptac promoter, a root-cell promoter, an ABA-inducible promoter and a turgor-inducible promoter.

Further, in another example of the expression cassette of the present invention is as described above for the SOS2 mutants, but rather it contains a nucleic acid encoding a SOS3 protein of SEQ ID NO: 12 (e.g., a polynucleotide having the sequence of SEQ ID NO: 11), wherein enhanced expression of the protein in a plant cell expressing a SOS2 mutant of the present invention imparts increased salt tolerance to said plant cell.

In yet another embodiment, the expression cassette may contain both polynucleotides encoding a SOS2 mutant of the present invention and SOS3 (these polynucleotides and the variants thereof are described below), either under the control of the same promoter or a selectively inducible promoter, on the same (or different) plasmid or vector.

As used herein the term "selectively inducible promoter" means that when two or more promoters are present on the same plasmid or vector, or when these promoters are present on a different plasmid or vector but the plasmids or vectors are contained in the same host cell, plant cell, or transgenic plant, these promoters are compatible with the host (stably maintained by the host cell, plant cell, or transgenic plant) and may be individually activated or transcription enhanced (e.g., by addition of IPTG in the case of one promoter and by an increase in temperature in another).

Although T/DSOS2 (polynucleotide sequence=SEQ ID NO: 3; protein sequence=SEQ ID NO: 4), T/DSOS2/308 (polynucleotide sequence=SEQ ID NO: 5; protein sequence=SEQ ID NO: 6), T/DSOS2/329 (polynucleotide sequence=SEQ ID NO: 7; protein sequence=SEQ ID NO: 8), and T/DSOS2DF (polynucleotide sequence=SEQ ID NO: 9; protein sequence=SEQ ID NO: 10) represent the preferred mutant forms of SOS2, it is also envisioned that the scope of the SOS2 present invention is not limited to these mutant forms. Within the scope of the present invention, it is also possible to use the aforementioned mutant forms of SOS2 as the linchpin for additional mutants.

Clearly, it is within the scope of the present invention to utilize silent mutants at a nucleic acid level. In other words, the present invention also relates to coding DNA sequences, which result from the aforementioned sequences by degeneration of the genetic code. In the same manner, the invention further relates to DNA sequences that hybridize with the sequences of the present invention, or with parts of said sequences, under stringent conditions. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral mutations.

A gene can also be used which encodes a corresponding or variant enzyme (e.g., SOS2 and/or SOS3) with a high activity. Preferably, the corresponding enzyme has a greater activity than the form of the enzyme from which it is derived, more preferably at least in the range of 5, 10, 25% or 50% more activity, most preferably more than twice the activity of the enzyme from which it is derived.

In the context of the present application, a polynucleotide sequence is "homologous" with the sequence according to the present invention if at least 70%, preferably at least 80%, more preferably at least 90%, most preferably at least 95% of its base composition and base sequence corresponds to the sequence according to the invention. According to the invention, a "homologous protein" is to be understood to comprise proteins which contain an amino acid sequence at least 70%, preferably at least 80%, more preferably at least 90%, most preferably at least 95% of which, corresponds to the amino acid sequence according to the present invention or which is encoded by the aforementioned polynucleotide sequence, wherein "corresponds" is to be understood to mean that the corresponding amino acids are either identical or are mutually homologous amino acids.

As set forth herein, the sequences of the present invention correspond to: T/DSOS2 (polynucleotide sequence=SEQ ID NO: 3; protein sequence=SEQ ID NO: 4), T/DSOS2/308 (polynucleotide sequence=SEQ ID NO: 5; protein sequence=SEQ ID NO: 6), T/DSOS2/329 (polynucleotide sequence=SEQ ID NO: 7; protein sequence=SEQ ID NO: 8), and T/DSOS2DF (polynucleotide sequence=SEQ ID NO: 9; protein sequence=SEQ ID NO: 10). When homologous polynucleotides and/or proteins to the foregoing are employed, these sequences should encode for a protein possessing or should possess, respectively, serine/threonine kinase activity. In certain embodiments of the present invention, also included is the calcium binding protein SOS3 having a native polynucleotide sequence of SEQ ID NO: 11 and an protein sequence of SEQ ID NO: 12. Of course, the present invention embraces the full range of homologues of the same.

The expression "homologous amino acids" denotes those that have corresponding properties, particularly with regard to their charge, hydrophobic character, steric properties, etc. Thus, the protein may be from 70% up to less than 100% homologous to the aforementioned sequences.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides that contain the complete gene with the polynucleotide sequence corresponding to SEQ ID NOs: 3, 5, 7, or 9, or fragments thereof, and which can be obtained by screening by means of the hybridization of a corresponding gene bank with a probe which contains the sequence of said polynucleotide corresponding to SEQ ID NOs: 3, 5, 7, or 9, or fragments thereof, and isolation of said DNA sequence.

Polynucleotide sequences according to the invention are suitable as hybridization probes for RNA, cDNA and DNA, in order to isolate those cDNAs or genes which exhibit a high degree of similarity to the sequence of the mutant SOS2 genes, in particular the mutant SOS2 genes of SEQ ID NOs: 3, 5, 7, or 9.

Polynucleotide sequences according to the invention are also suitable as primers for polymerase chain reaction (PCR) for the production of DNA that encodes an enzyme having SOS2 serine/threonine kinase activity.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment. It is to be understood that the "isolated" polynucleotides and polypeptides of the present invention may further be substantially pure or pure (i.e., the polynucleotides and polypeptides have been purified). As used herein, the term "substantially pure" means that the polynucleotides and polypeptides have been isolated from its natural environment to an extent such that only minor impurities remain (e.g., the resultant polynucleotides and polypeptides are at least 70%, preferably at least 80%, more preferably at least 90%, most preferably at least 95% pure). As used herein, the term "pure" means that the polynucleotides and polypeptides are free from contaminants (i.e., are 100% pure).

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins, which contain two or more amino acids which are bound via peptide bonds.

The polypeptides according to invention include polypeptides corresponding to SEQ ID NOs: 4, 6, 8, or 10, particularly those with the biological activity of a SOS2 serine/threonine kinase activator, and also includes those, at least 70% of which, preferably at least 80% of which, more preferably at least 90% of which, most preferably at least 95% of which, are homologous with the polypeptide corresponding to SEQ ID NOs: 4, 6, 8, or 10, and which have the cited activity. Thus, the polypeptides may have a homology of from 70% up to 100% with respect to SEQ ID NOs: 4, 6, 8, or 10.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40% to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Specificity" is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)-0.61 (% form)-500/L; where M nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolate polynucleotides that are substantially similar to the present polynucleotides. In so isolating such a polynucleotide, the polynucleotide can be used as the present polynucleotide in, for example, increasing salt tolerance of a plant.

It is also conceivable within the scope of the present invention that the skilled artisan may utilize fragments of the mutant SOS2 proteins to screen for polynucleotides that have substantial homology to the polynucleotides of the present invention, preferably those polynucleotides encoding a protein having SOS2 serine/threonine kinase activity.

The polynucleotide sequences of the present invention can be carried on one or more suitable plasmids or vectors (e.g., an expression vector), as known in the art for plants or the like. As stated above, it is also within the scope of the present invention to have the polynucleotide sequences (e.g., one of SEQ ID NOs: 3, 5, 7, or 9 and SEQ ID NO: 11) on the same or different plasmids or vectors. In an embodiment of the present invention, these polynucleotides may be operably linked to a single promoter, different promoters of the same type, or selectively inducible promoters, on the same (or different) plasmid or vector.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

In an embodiment of the present invention, the polynucleotides of the present invention (i.e., the SOS2 mutants, variants thereof, as described above) are contained in a plasmid or vector either in the absence of presence of a polynucleotide relating to SOS3 or a variant thereof (as described above).

In another embodiment of the present invention, the plasmid(s) or vector(s) of the present invention are contained in a host cell, a plant cell, or a transgenic plant. Preferably, the plant is *Arabidopsis thaliania* or selected from the group consisting of wheat, corn, peanut cotton, oat, and soybean plant. In a preferred embodiment, the polynucleotides of the present invention are operably linked to a promoter, preferably an inducible promoter. As described hereinabove, the polynucleotides may be operably linked to a single promoter, different promoters of the same type, or selectively inducible promoters, on the same (or different) plasmid or vector.

In another preferred embodiment, the present invention provides a method of making a transgenic plant comprising introducing the polynucleotides of the invention into the plant.

In another preferred embodiment, the present invention provides method of increasing salt tolerance of a plant in need thereof, comprising introducing the polynucleotides (inclusive of the polynucleotides defined herein for SOS2 alone or in the presence of the polynucleotides defined herein for SOS3) of the invention into said plant.

In a preferred embodiment, the plant cells in which said overexpression occurs is in the shoot or root of the plant, more preferably in the shoot of the plant.

Methods, vectors, and compositions for transforming plants and plant cells in accordance with the invention are well-known to those skilled in the art, and are not particularly limited. For a descriptive example see Karimi et al., TRENDS in Plant Science, Vol. 7, NO: 5, May 2002, pp. 193-195, incorporated herein by reference. Further, this method entails inducing expression of the respective genes by subjecting the plant containing the vectors of the present invention for a sufficient time and under conditions suitable to impart salt sensitivity to said plant. The time and conditions may be empirically determined. However, it should be understood that basal expression of the genes of the present invention may be sufficient to support and/or impart increased salt tolerance upon a plant containing the same.

In yet another embodiment of the present invention, the transgenic plant described above may contain the aforementioned genes for the SOS2 mutants may be integrated into the genome of the transgenic plant. Methods for genomic integration are well-known to the skilled artisan.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods

Preparation of Active SOS2 Kinase Expression Plasmids and Plant Transformation:

T/DSOS2 (polynucleotide sequence=SEQ ID NO: 3; protein sequence=SEQ ID NO: 4), T/DSOS2/308 (polynucleotide sequence=SEQ ID NO: 5; protein sequence=SEQ ID NO: 6), and T/DSOS2/329 (polynucleotide sequence=SEQ ID NO: 7; protein sequence=SEQ ID NO: 8) were obtained as described in Guo et al., 2001 (incorporated herein by reference in its entirety), while T/DSOS2DF (polynucleotide sequence=SEQ ID NO: 9; protein sequence=SEQ ID NO: 10) was obtained as described in Qiu et al, 2002 (incorporated herein by reference in its entirety). Native SOS2 has the polynucleotide sequence of SEQ ID NO: 1 and the protein sequence of SEQ ID NO: 2, while native SOS3 has the polynucleotide sequence of SEQ ID NO: 11 and the protein sequence of SEQ ID NO: 12.

For expression of constitutively active SOS2 kinase in *A. thaliana*, DNA fragments of T/DSOS2, T/DSOS2/308, T/DSOS2/329, and T/DSOS2DF were digested from their GST fusion constructs (Guo et al., 2001) with BamHI and EcoRI and cloned into a binary vector (pCAMBIA1027) under the control of the CaMV 35S promoter. The plasmids were introduced into *Agrobacterium tumefaciens* strain GV3101 by electroporation and then transferred into wild-type (*A. thaliana* Columbia ecotype), sos2-2, or sos3-1 mutant plants by vacuum infiltration. Hygromycin-resistant transgenic T2 and T3 plants were tested for growth in salt.

Growth Measurements:

Seeds of wild-type, sos2-2, sos3-1, and transgenic plants were surface-sterilized in 7% (w/v) hypochlorite and 0.01% (w/v) Triton X-100 and then rinsed five times with sterile water. The seeds were sown on an MS nutrient medium (JRH Biosciences, Lenexa, Kans.) containing 0.6% agar and the indicated NaCl concentrations. The seeds were stratified at 4° C. for 3 days and then transferred to 22° C. under continuous light for measurements of germination and growth.

For seedling growth in salt, 5-day-old seedlings of wild-type, sos2-2, sos3-1, and transgenic plants were transferred to MS medium containing 1.2% agar and the indicated NaCl concentrations. Growth was monitored using a root bending assay (Zhu et al., 1998). Plant salt tolerance in soil was assayed as described in Shi et al. (2003).

RNA Analysis:

Total RNA was extracted from 2-week-old seedlings, and 40 μg of each sample was used for RNA analysis as described (Guo et al., 2001).

Immunoblot Analysis and Kinase Assays

Total proteins (5 g from 10-d-old seedlings) were extracted at 4° C. from wild-type, sos2-2, sos3-1, and transgenic plants in 10 mL 1×PBS buffer (137 mM NaCl, 2.7 mM KCl, 4.3 mM Na2HPO4, and 1.4 mM NaH2PO4, pH 7.4) with 5 mM dithiothreitol, 2 μg aprotinin mL-1, 2 μg leupeptin mL-1, and 2 mM phenylmethanesulfonyl fluoride. To isolate sufficient amounts of T/DSOS2 protein, GST-SOS3 fusion protein (Halfter et al., 2000) was first purified using glutathione-Sepharose beads (Amersham Pharmacia Biotech, Uppsala, Sweden). Total *A. thaliana* proteins were then incubated with 100 μL of GST-SOS3 coupled to the Sepharose beads for 2 hours at 4° C. The GST-SOS3 beads-T/DSOS2 protein complex was washed three times with 1×PBS buffer. Ten microliters of the protein complex were used for either immunoblot analysis or protein kinase assays.

For immunoblot analysis, 3 μL of 3× protein loading buffer (200 mM Tris-HCl, pH 6.8, 8% SDS, 30% glycerol, 1.5% β-mercaptoethanol, and 0.3% bromophenol blue) were added to 10 μL protein, and the samples were boiled for 5 min. The samples were run on a 10% SDS-PAGE gel, and the proteins were transferred to a pure nitrocellulose membrane (Bio-Rad Laboratories, Hercules, Calif.) at 80 V for 60 min. The membrane was blocked overnight at 4° C. in 1×PBS buffer with 5% fat-free milk, rinsed one time with 1×PBS, and incubated with SOS2 antibodies (diluted 1:1000) for 3 hours at room temperature. After three washes with 1×PBS buffer, the membrane was incubated with anti-rabbit IgG secondary antibody (Amersham Biosciences, Piscataway, N.J.) diluted 1:2500 for 1 hour at room temperature. The membrane was then washed five times with 1×PBS and the immunoreactive bands detected using the chemiluminescent ECL detection substrate (Amersham Biosciences).

Ten microliters of SOS3-T/DSOS2 beads were used for p3 peptide phosphorylation assays as described by Halfter et al. (2000).

Na+/H+ Exchange:

Plasma membrane vesicles were isolated using aqueous two-phase partitioning as described (Qiu and Su, 1998; Qiu et al., 2002). Na+/H+ exchange (antiport) activity was measured as a Na+-induced dissipation of the pH gradient (ΔpH, i.e., a Na+-induced increase in quinacrine fluorescence; Qiu et al., 2002). When ΔpH reached steady state, NaCl was added to initiate Na+ transport. To determine initial rates of Na+/H+ exchange (change in fluorescence per minute; Δ%F min−1), changes in relative fluorescence were measured during the first 15 s after addition of Na+. Specific activity was calculated by dividing the initial rate by the mass of plasma membrane protein in the reaction (Δ%F mg−1 protein min−1). To determine whether T/DSOS2 activated SOS1 in vitro, 200 ng of T/DSOS2 protein was preincubated with wild-type membrane vesicles for 7 min at room temperature before the antiport activity assays.

Yeast Growth

The *S. cerevisiae* strain YP890 is a derivative of AXT3K (Δena1:HIS3:ena4, nha1:LEU2, and nhx1:KanMX) (Quintero et al., 2002), in which a PGK1:SOS1:CYC1 expression cassette was inserted at the 3' untranslated region of the chromosomal gene CYC1. The chromosomal placement of the transgene and the use of the PGK1 promoter provide moderate and constitutive expression of the *A. thaliana* SOS1 protein in YP890 cells. The plasmids that contain either wild-type SOS2, activated forms of SOS2 (T/DSOS2, T/DSOS2/308, T/DSOS2/329, and T/DSOS2/DF), or the inactive SOS2 mutant bearing substitution Lys40 to Asn (T/DSOS2/KN) were made by inserting BamHI-EcoRI fragments from pGEX-SOS2 derivatives (Guo et al. 2001) into the BamHI-EcoRI sites of the p414GPD vector. The cDNAs of wild-type SOS3 and mutant sos3-1 were cloned into the XbaI-XhoI sites of the expression vector pYPGE15. Transformation of S. cerevisiae was performed using a standard lithium-polyethylene glycol method. The ability of S. cerevisiae to grow in salt was tested on AP medium, which is essentially free of alkali cations. Strains were cultured overnight in liquid AP medium supplemented with 1 mM KCl. After harvest, cells were resuspended and diluted decimally in distilled water. Aliquots (5 µL) were spotted onto AP plates supplemented with 1 mM KCl and various concentrations of NaCl, as noted, and grown for 3 to 4 days at 28° C.

SRS:

Plasmid pSRS2-1 containing the gene fusion hSos:SOS2 was used to monitor plasma membrane targeting of SOS2 (Quintero et al., 2002). SOS3 and sos3-1 were expressed using the vector plasmid pYPGE15 as described above. All plasmids used for SRS were transformed into the S. cerevisiae strain Cdc25-2 (Mat⊐, cdc25-2, ura3, lys2, leu2, trp1, his3, and ade101), which is conditional lethal at 37° C. unless the fusion protein hSos:SOS2 reaches the plasma membrane (Aronheim et al., 1997). Cell viability at 37° C. was determined in YPD plates (1% yeast extract, 2% peptone, and 2% glucose).

Results

Changes in the SOS2 Protein Produce Constitutively Active Kinases

Based on its inability to autophosphorylate or phosphorylate a peptide substrate, SOS2 appears to be an inactive kinase. The calcium binding protein SOS3 has been shown to interact with and activate SOS2 in vitro in the presence of calcium (Halfter et al., 2000). The present inventors have previously shown that SOS2 kinases that are active in the absence of SOS3 and calcium (constitutively active SOS2) could be produced either by exchange of $Thr^{168}$ in the activation loop to the acidic residue Asp (T/DSOS2) or by deletion of the FISL motif in the C-terminal regulatory domain of the SOS2 protein (SOS2DF) (Guo et al., 2001; Qiu et al., 2002), and that a superactive SOS2 kinase could be generated by combining these two changes (T/DSOS2DF) (Qiu et al., 2002).

In this study, additional changes were made to the SOS2 kinase to allow the development of a series of SOS2 proteins for studies of SOS2 structure and function. The FISL motif and C-terminal 117 amino acids or the C-terminal 117 amino acids were removed in the glutathione S-transferase (GST)-T/DSOS2/308 and GST-T/DSOS2/329 constructs, respectively (FIG. 1A). These proteins were assayed for autophosphorylation or their ability to phosphorylate a peptide substrate, and their activities compared with those of the wild-type SOS2 protein, T/DSOS2, or T/DSOS2DF. T/DSOS2/308 had the strongest activities, followed by T/DSOS2DF, T/DSOS2, T/DSOS2/329, and SOS2 (FIGS. 1B to 1D). These kinase constructs served as the basis of the following transgenic studies in S. cerevisiae and A. thaliana.

The Protein Kinase Activity of SOS2 is Partially Sufficient for Salt Tolerance In Vivo in a Heterologous System Recently, the A. thaliana SOS regulatory pathway has been reconstituted in S. cerevisiae (Quintero et al., 2002), providing an in vivo system for studies of SOS2 structure-function relationships. To determine if the kinase activity of SOS2 correlates with activation of SOS1, wild-type and constitutively active SOS2 kinases were introduced into S. cerevisiae strain YP890, in which the endogenous S. cerevisiae $Na^+$ transporters ($Na^+$ efflux proteins ENA1-4 and NHA1 and the vacuolar $Na^+/H^+$ exchanger NHX1) had been removed and the A. thaliana SOS1 gene was constitutively expressed from a chromosomal insertion. The transformed S. cerevisiae strains were grown on Arg phosphate (AP) medium containing 1 mM KCl and various concentrations of NaCl, and the results are shown in FIG. 2.

The low basal activity of SOS1 and the moderate level of expression achieved in strain YP890 failed to support cell growth above 50 mM NaCl (data not shown). The salt tolerance of YP890 was not substantially enhanced by the expression of the wild-type SOS2 (FIG. 2A) but was dramatically increased by the coexpression of the SOS2-SOS3 kinase complex.

There was no further increase in salt tolerance when T/DSOS2, bearing the $Thr^{168}$-to-Asp mutation that mimicked the phosphorylated state of SOS2 (Gong et al., 2002), was expressed in place of the wild-type SOS2 (FIG. 2). By contrast, a $Lys^{40}$-to-Asn mutation in the catalytic site required for phosphotransfer activity (Gong et al., 2002) produced an inactive kinase (T/DSOS2/KN), even in the presence of SOS3.

Expression T/DSOS2/308, with a truncation that removed the entire autoinhibitory C-terminal part of SOS2, strongly enhanced the ability of S. cerevisiae to grow in NaCl in the absence of SOS3, and coexpression of SOS3 failed to increase salt tolerance further because of lack of interaction between these two proteins. Deletion of the FISL motif (T/DSOS2DF) partially released SOS2 from autoinhibition, as did the truncation in T/DSOS2/329 that removed the last 117 C-terminal amino acids but retained the FISL domain. However, although SOS3 cooperated with T/DSOS2/329 through the FISL domain to activate SOS1, coexpression of SOS3 had no effect on T/DSOS2DF (FIG. 2A). The greater salt tolerance imparted by T/DSOS2/308 relative to T/DSOS2DF and T/DSOS2/329 in the absence of SOS3, together with data shown in FIG. 1, indicate that the entire C-terminal part of SOS2 may contribute to autoinhibition of the kinase activity.

Figure 1:
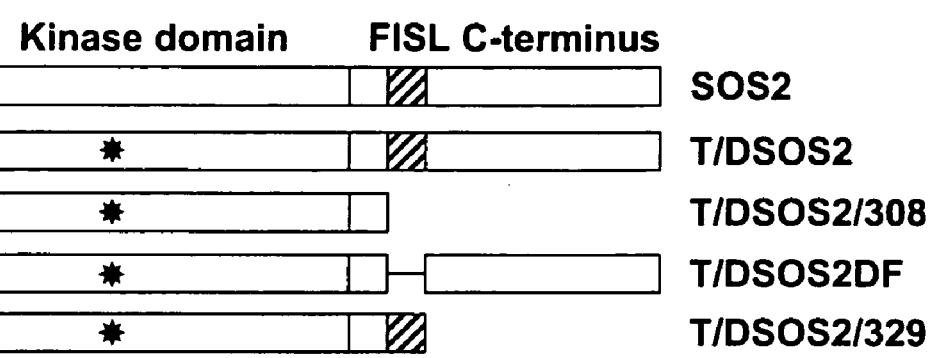
FIG. 1: Active SOS2 Kinases.
Figure 1:
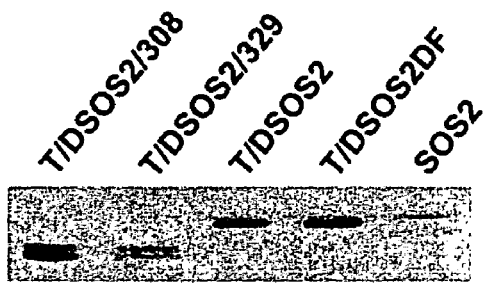
Figure 1:
Figure 1:
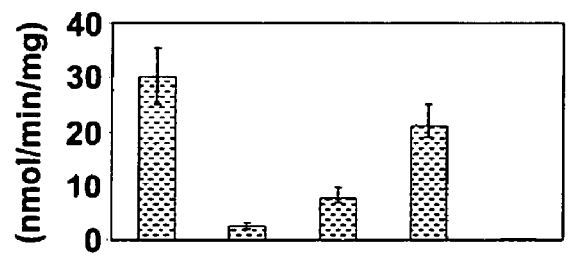

In the presence of SOS3, both T/DSOS2/308 and T/DSOS2/329 performed similarly regarding SOS1 activation (FIG. 2A), despite their significantly different kinase and autophosphorylation activities in vitro (FIG. 1). Together, these results demonstrate that the kinase activity determined in vitro correlates well with functionality of SOS2 in vivo and in the absence of SOS3, but they also illustrate that the capacity for binding SOS3 and recruitment to the plasma membrane is critical for the competence of SOS2 for SOS1 activation. On the other hand, none of the SOS2 kinases activated through protein truncation could increase the salt tolerance of S. cerevisiae to the same level achieved when SOS1 was coexpressed with SOS2 and SOS3 proteins retaining structural integrity, indicating that interaction between the full-length polypeptides is optimal for function.

The sos3-1 mutation of A. thaliana causes deletion of three conserved amino acids in a central EF hand (Liu and Zhu, 1998). Although the present inventors have shown previously that the sos3-1 mutation drastically reduces the capacity of SOS3 to activate SOS2 in vitro (Ishitani et al., 2000), the present inventors tested if the SOS3-1 polypeptide could still interact in vivo with activated SOS2 proteins retaining the FISL motif and recruit them to the plasma membrane. Alleles SOS2 and T/DSOS2 were coexpressed with the cDNA of sos3-1 in YP890 cells. As shown in FIG. 2B, the SOS3-1 mutant polypeptide failed to mediate activation of SOS1 by SOS2 or T/DSOS2. In addition, using the SOS Recruitment System (SRS) to monitor targeting of SOS2 to the plasma membrane (Quintero et al., 2002), the present inventors determined that SOS3-1 was unable to recruit SOS2 or T/DSOS2 to the plasma membrane (FIG. 2C).

The Protein Kinase Activity of SOS2 is Partially Sufficient for Salt Tolerance in Planta To determine if the protein kinase activity of SOS2 is sufficient for salt tolerance in planta, the wild-type and the constitutively active forms of SOS2 were expressed under the 35S promoter of Cauliflower mosaic virus (CaMV) in the sos2 and sos3 mutants of *A. thaliana*. Five-day-old T2 transgenic plants expressing 35S:SOS2 (germinated on MS medium without salt) were transferred to plates with either MS medium or MS medium with 100 mM NaCl. Three of twelve independent T2 transgenic lines in the sos2-2 background evaluated had salt tolerance nearly restored to levels equivalent to that of the wild type. By contrast, none of the 24 independent transgenic lines in the sos3-1 background evaluated showed any increased salt tolerance relative to the sos3-1 mutant.

One representative T3 homozygous 35S:SOS2 line in the sos3-1 and sos2-2 backgrounds was evaluated for SOS2 transcript accumulation and growth in salt (FIG. 3). RNA analysis indicated that the transgenic plants accumulated high levels of SOS2 mRNA from the transgene because the endogenous SOS2 expression was extremely low (FIG. 3E) and could only be seen with prolonged exposure of the blot (data not shown). The results show that ectopic expression of SOS2 under the CaMV 35S promoter could rescue the sos2-2 phenotype (FIG. 3B). As expected, the ectopic expression of SOS2 did not rescue the sos3-1 salt-hypersensitive phenotype (FIG. 3D), confirming that the wild-type SOS2 protein must be activated by SOS3 in vivo for function in *A. thaliana*.

Expression of active T/DSOS2 kinase in sos2-2 and sos3-1 resulted in 5 of 12 T2 sos2-2 transgenic lines and 4 of 12 T2 sos3-1 transgenic lines, in which the shoot sensitivity but not the root sensitivity of the mutant phenotype was rescued. RNA analysis demonstrated that the sos2-2 and sos3-1 transgenic plants accumulated a high level of T/DSOS2 transcript (FIG. 4A). SOS2 transcript and protein are in low abundance in *A. thaliana* and even when SOS2 transcript levels were higher because of the strong CaMV 35S promoter, SOS2 protein levels were still virtually undetectable using our SOS2 antisera (data not shown).

Therefore, to analyze the levels of T/DSOS2 protein in the transgenic plants, total proteins were extracted from mutants and transgenic plants, and SOS2 protein (from both endogenous SOS2 and 35S:T/DSOS2) was enriched based on its binding to SOS3. The proteins were loaded onto a column containing GST-SOS3 fusion protein that was bound to glutathione-Sepharose beads. The resulting GST-SOS3-SOS2 or T/DSOS2 complexes were used for either immunoblot analysis or peptide phosphorylation assays. As shown in FIG. 4B, expression of T/DSOS2 in either sos2-2 or sos3-1 resulted in the accumulation of T/DSOS2 protein at higher levels than the preexisting SOS2 protein levels in the sos2-2 and sos3-1 mutants. Based on phosphorylation of the p3 peptide, T/DSOS2 kinase activity from both the sos2-2 and sos3-1 transgenic plants was approximately four times higher than in the corresponding mutants (FIG. 4C). Because several PKS (SOS2-like protein kinases) proteins also interact with SOS3 (Guo et al., 2001), the kinase activities from the untransformed mutants may not represent the activity of only SOS2.

Five-day-old seedlings of wild-type, mutant, and T/DSOS2 transgenic plants were transferred to either MS medium or MS medium containing 100 mM NaCl. No significant differences in plant growth were observed on MS medium (FIG. 5A). When the plants were grown on medium containing 100 mM NaCl, the growth of the wild-type plants was retarded but root bending was largely unaffected, whereas growth of sos2-2 and sos3-1 was severely inhibited (FIG. 5B) and plants died within 2 weeks (data not shown). Expression of T/DSOS2 in sos2-2 was able to partially rescue the shoot salt hypersensitivity but not the root salt hypersensitivity (FIG. 5B).

These results suggest that in the shoot, ectopic expression of T/DSOS2 partially restored salt tolerance in the sos2-2 background. Expression of T/DSOS2 in sos3-1 was also able to partially rescue the shoot salt hypersensitivity but not the root salt hypersensitivity (FIGS. 5B and 5C), suggesting that in the shoot, addition of the active kinase partially bypassed the requirement for SOS3.

No differences in either vegetative or reproductive growth were seen when mutant and transgenic plants grown in soil were watered with 0.05×MS nutrients in the absence of NaCl (data not shown). However, when the plants were treated with NaCl, sos2-2 and sos3-1 lost vigor faster, and both vegetative and reproductive growth decreased (FIGS. 5D and 5E). Expression of T/DSOS2 improved the growth of the mutants under NaCl stress (FIGS. 5D and 5E), although it did not restore salt tolerance to wild-type levels (data not shown).

The Protein Kinase Activity of SOS2 May be Lmiting for Salt Tolerance in *Arabidopsis thaliana*

To determine if levels of SOS2 protein are limiting in vivo and if increasing active SOS2 levels lead to improved salt tolerance in planta, SOS2 and T/DSOS2 were expressed in wild-type plants under the control of the CaMV 35S promoter. Of 24 T2 35S:SOS2 transgenic lines evaluated, all had levels of salt tolerance similar to that in the untransformed wild type. The levels of SOS2 transcript were determined in three T3 homozygous 35S:SOS2 lines and strong expression was detected in all the transgenic plants (FIG. 6A). The salt tolerance of two of these lines was subsequently evaluated during germination (FIGS. 6B and 6C) and seedling growth (FIGS. 6D to 6F); responses to salt at both stages were similar to those in the wild type. The lack of enhancement of salt tolerance in plants overexpressing wild-type SOS2 indicates that SOS2 protein levels are not limiting in *A. thaliana* in vivo.

Exchange of $Thr^{168}$ in the activation loop of the SOS2 protein with Asp mimics the phosphorylation of $Thr^{168}$ by an unknown upstream kinase and leads to activation of SOS2 (Guo et al., 2001). When T/DSOS2 was expressed in wild-type plants, 7 of 34 T2 transgenic lines evaluated showed increased salt tolerance compared with untransformed wild-type plants. Two of the seven T3 homozygous 35S:T/DSOS2 lines were analyzed for T/DSOS2 transcript and protein accumulation and salt tolerance. The transgenic plants accumulated high levels of T/DSOS2 transcript and protein (FIGS. 7A and 7B). T/DSOS2 kinase activity from the transgenic plants was enhanced four to five times over the kinase activity levels in the wild type (FIG. 7C). No difference was seen when seeds from transgenic or wild-type plants were germinated on MS medium without salt (FIG. 8A, left panel).

However, seeds from the transgenic lines showed more rapid germination on MS medium containing 100 mM NaCl (FIG. 8A, right panel), and seedling development proceeded further in salt (green cotyledons developed) in the transgenic plants. Growth of wild-type and transgenic seedlings in the absence of salt was similar (FIG. 8B, top panel). However, when seedlings were transferred to medium with NaCl, the transgenic plants showed significantly less growth inhibition, which was especially evident at 120 mM NaCl (FIG. 8B, middle and bottom panels).

To test the salt tolerance of the plants when grown in soil, wild-type and transgenic seeds were germinated in soil and watered with 0.05×MS nutrients. After 3 weeks, the plants were treated with NaCl by progressively increasing the NaCl concentration 50 mM every 4 d until a final concentration of 200 was reached (Shi et al., 2003). The transgenic plants showed improved vegetative and reproductive growth in soil with 200 mM NaCl when compared with growth of the wild-type plants (FIG. 8C); no difference was found when plants were grown without NaCl (data not shown). The increased salt tolerance of the plants expressing the T/DSOS2 kinase suggests that levels of activated kinase may be limiting in *A. thaliana* in vivo and that increasing active SOS2 levels in planta can lead to improved salt tolerance.

Enhancement of SOS1 Activity In Vivo by Constitutively Active SOS2

Previous studies have shown that active SOS2 protein stimulates the $Na^+/H^+$ antiport activity of SOS1 in vitro (Qiu et al., 2002), suggesting that SOS2 directly regulates the activity of SOS1. To determine if in vivo SOS2 kinase activity is sufficient to regulate SOS1 activity and if SOS1 activation might contribute to the improved salt tolerance conferred by T/DSOS2, the present inventors measured SOS1 transport activity in the 35S:T/DSOS2 transgenic plants and the untransformed wild-type, sos2-2, and sos3-1 control plants.

For these studies, highly purified plasma membrane vesicles were isolated from wild-type, sos2-2, sos3-1, and their T/DSOS2 transgenic plants after treatment with 250 mM NaCl for 3 d. When T/DSOS2 protein was added in vitro to plasma membrane vesicles isolated from untransformed wild-type plants, $Na^+/H^+$-exchange activity increased with increasing NaCl concentration and was higher than activity in the absence of T/DSOS2 protein at all NaCl concentrations (FIG. 9A). A maximum stimulation of activity of 40% relative to activity without added protein was measured with 100 mM NaCl. $Na^+/H^+$ exchange activity, measured in vesicles isolated from T/DSOS2 transgenics of the wild-type, sos2, and sos3 plants, was higher than in the respective untransformed controls (FIGS. 9B to 9D); however, the exchange activity of the sos2-2 and sos3-1 transgenic lines was restored to only half to two-thirds of the levels of activity measured in the untransformed wild type, in agreement with the partial suppression of their salt sensitivity (FIG. 5).

These results demonstrate that expression of the active kinase T/DSOS2 enhanced SOS1 activity in vivo in the transgenic plants. These measurements also provide further evidence that more than SOS2 is required for full SOS1 activity and salt tolerance in vivo. Besides activating SOS1, expression of the active kinase may also enhance salt tolerance through other mechanisms (e.g., enhancement of vacuolar $Na^+/H^+$ antiport activity) because SOS2 has been shown to be a regulator of vacuolar $Na^+/H^+$ antiporters (Qiu et al., 2004).

The C-Terminal Region of SOS2 is Required for Function in Planta

The above experiments showed that the active kinase T/DSOS2 could enhance SOS1 activity and salt tolerance when expressed either in wild-type, sos2, or sos3 plants. Because T/DSOS2/308 (with the $Thr^{168}$-to-Asp change and in which the FISL domain and C-terminal 117 amino acids were removed) exhibited the highest protein kinase activity in vitro (FIG. 1) and was the most competent for activation of SOS1 in *S. cerevisiae* in the absence of SOS3 (FIG. 2), T/DSOS2/308 was expressed in the sos2-2 or sos3-1 mutants under the CaMV 35S promoter. Twenty-four independent T2 transgenic lines from each transformation were tested for growth in salt; none had salt tolerance that was greater than that of either the sos2-2 or sos3-1 mutant. One representative T3 homozygous line from expression of T/DSOS2/308 in sos2-2 (FIGS. 10A and 10B, top) and sos3-1 (FIGS. 10A and 10B, bottom) is shown. Although the transgene was expressed at high levels in the transgenic plants (FIG. 10C), salt tolerance was not enhanced. These results suggest that the FISL motif and/or the C-terminal 117 amino acids are required for salt tolerance in planta.

Compared with T/DSOS2/308, T/DSOS2/329 (with the $Thr^{168}$-to-Asp change and in which the C-terminal 117 amino acids were removed) contains the FISL motif but is not as active because the FISL motif is inhibitory to SOS2 activity (FIGS. 1 and 2). When 35S:T/DSOS2/329 was expressed in the sos2-2 or sos3-1 mutants, salt tolerance was not restored. One representative T3 homozygous line from expression of T/DSOS2/329 in sos2-2 (FIGS. 10D and 10E, top) and sos3-1 (FIGS. 10D and 10E, bottom) is also shown. As with T/DSOS2/308, expression of the transgenes was high in the transgenic plants (FIG. 10F), but salt tolerance was not enhanced. The data from the analysis of the sos2-2 and sos3-1 transgenic lines expressing T/DSOS2/329 suggest that adding back the FISL motif is not sufficient to restore the function to the active T/DSOS2/308 kinase in planta. Together with the data from the T/DSOS2/308 expressing transgenic plants, the results reveal a critical role for the C-terminal region of SOS2 in salt tolerance in planta.

To further examine the role of the FISL motif and the C-terminal 117 residues, T/DSOS2DF (with the $Thr^{168}$-to-Asp change and in which the FISL domain was removed) was expressed in the wild-type *A. thaliana* and the sos2-2 or sos3-1 backgrounds. When T/DSOS2DF was expressed in the wild-type plants, 4 of 12 of T2 transgenic lines evaluated were more salt tolerant than the untransformed wild type. The levels of T/DSOS2DF transcript were determined in two T3 homozygous lines, and high accumulation in both was detected (FIG. 11A). When these plants were evaluated for salt tolerance during germination and seedling growth, no significant differences in germination were detected on medium without salt (FIG. 11B). By contrast, the transgenic plants had faster germination and improved seedling development on MS medium containing 100 mM NaCl (FIG. 11C). When 5-d-old seedlings were transferred to MS medium, the growth of wild-type and transgenic plants was similar (FIG. 11D). When seedlings were transferred to MS medium containing 100 mM or 120 mM NaCl, growth of the transgenic plants was less inhibited by NaCl (FIGS. 11E and 11F).

The present inventors attempted to enrich the T/DSOS2DF protein by incubating total protein extracts (from a transgenic line with increased salt tolerance) with GST-SOS3 on glutathione-Sepharose beads. However, T/DSOS2DF protein could not be detected by immunoblot analysis (data not shown), and no T/DSOS2DF kinase activity was detected in peptide phosphorylation assays (data not shown), indicating that T/DSOS2DF did not interact with SOS3 and further supporting previous interaction studies suggesting that the FISL motif is required for SOS2/SOS3 interaction.

When T/DSOS2DF was expressed in the sos2-2 and sos3-1 backgrounds, 3 of 12 T2 sos2-2 transgenic lines had salt tolerance that was restored almost to wild-type levels. However, of the 24 T2 sos3-1 transgenic lines evaluated, all had the sos3-1 phenotype with only slight root bending. Representative T3 homozygous sos2-2 and sos3-1 transgenic lines are shown in FIG. 12. The T/DSOS2DF transcript was detected in both transgenic lines (FIG. 12F). When 5-d-old seedlings from the wild-type, sos2-2, sos3-1, and transgenic sos2-2 or sos3-1 lines were transferred to MS medium without salt, no significant differences in growth were found (FIGS. 12A and 12C). However, when the seedlings were transferred to MS medium containing 100 mM NaCl, sos2-2 plants died within 2 weeks, whereas the phenotype of the sos2-2 transgenic plants was similar to the wild type but with slightly smaller shoots and fewer lateral roots (FIG. 12B). Expression of T/DSOS2DF in sos3-1 led to a slight increase in root elongation relative to sos3-1 when plants were grown on 100 mM NaCl (FIGS. 12D and 12E); however, both sos3-1 and the sos3-1 transgenic lines were unable to survive on this medium for >2 weeks.

The results with the 35S: T/DSOS2DF transgenic plants demonstrate that the 117 residues C terminal to the FISL motif are necessary and sufficient for the in planta function of the active SOS2 kinase proteins in wild-type and sos2-2 mutant plants. However, function of the active kinase in sos3-1 mutant plants appears to require the FISL motif as well. Improved salt tolerance in the wild-type transgenic plants provides further support that the kinase activity of SOS2 is limiting in vivo, and increasing this activity can be beneficial for salt tolerance.

The activity and functionality of the different forms of SOS2 in vitro, in *S. cerevisiae*, and in wild-type and mutant *A. thaliana* is summarized in Table 1.

Numerous modifications and variations on the present invention are possible in light of the above teachings. It is, therefore, to be understood that within the scope of the accompanying claims, the invention may be practiced otherwise than as specifically described herein.

REFERENCES

Amtmann, A., and Sanders, D. (1999). Mechanisms of $Na^+$ uptake by plant cells. Adv. Bot. Res. 29, 76-112.

Apse, M. P., Aharon, G. S., Snedden, W. A., and Blumwald, E. (1999). Salt tolerance conferred by overexpression of a vacuolar $Na^+/H^+$ antiport in *Arabidopsis*. Science 285, 1256-1258.

Aronheim, A., Zandi, E., Hennemann, H., Elledge, S. J., and Karin, M. (1997). Isolation of an AP-1 repressor by a novel method for detecting protein-protein interactions. Mol. Cell. Biol. 17, 3094-3102.

Epstein, E., Norlyn, J. D., Rush, D. W., Kingsbury, R. W., Kelley, D. B., Cunningham, G. A. & Wronn, A. F. (1980) Science 210, 399-404.

Gaxiola, R. A., Li, J., Undurraga, S., Dang, L. M., Allen, G. J., Alper, S. L., and Fink, G. R. (2001). Drought- and salt-tolerant plants result from overexpression of the $AVP1H^+$-pump. Proc. Natl. Acad. Sci. USA 98, 11444-11449.

Gilmour, S. J., Sebolt, A. M., Salazar, M. P., Everard, J. D., and Thomashow, M. F. (2000). Overexpression of the *Arabidopsis* CBF3 transcriptional activator mimics multiple biochemical changes associated with cold acclimation. Plant Physiol. 124, 1854-1865.

Gong, D., Guo, Y., Jagendorf, A. T., and Zhu, J. K. (2002). Biochemical characterization of the *Arabidopsis* protein kinase SOS2 that functions in salt tolerance. Plant Physiol. 130, 256-264.

Guo, Y., Halfter, U., Ishitani, M., and Zhu, J.-K. (2001). Molecular characterization of functional domains in the protein kinase SOS2 that is required for plant salt tolerance. Plant Cell 13, 1383-1399.

Halfter, U., Ishitani, M., and Zhu, J.-K. (2000). The *Arabidopsis* SOS2 protein kinase physically interacts with and is activated by the calcium-binding protein SOS3. Proc. Natl. Acad. Sci. USA 97, 3735-3740.

TABLE 1

Summary of the in vitro and in vivo activities of the wild-type and activated forms of SOS2

|  | Auto-phosphorylation | Peptide Phosphorylation | S. cerevisiae growth (in salt) | | A. thaliana growth (in salt) | | |
| --- | --- | --- | --- | --- | --- | --- | --- |
|  |  |  | +SOS3 | −SOS3 | sos2 | sos3 | WT |
| SOS2 | − | − | ++++ | − | + | − | − |
| T/DSOS2 | ++ | ++ | ++++ | − | + | + | + |
| T/DSOS2DF | ++ | +++ | + | + | + | − | + |
| T/DSOS2/329 | + | + | ++ | + | − | − | ND |
| T/DSOS2/308 | +++ | ++++ | ++ | ++ | − | − | ND |

The level of phosphorylation activity in vitro and relative salt tolerance in vivo are indicated for each SOS2 variant by the number of "+" symbols.
Minus symbol indicates undetectable phosphorylation or no growth.
ND, not determined;
WT, wild-type form of SOS2.
The designation "+SOS3" or "−SOS3" refers to the presence or absence of SOS3.
The designation "sos2" and "sos3" refer to mutant phenotypes (see Examples, supra).

Ishitani, M., Liu, J., Halfter, U., Kim, C.-S., Shi, W., and Zhu, J.-K. (2000). SOS3 function in plant salt tolerance requires N-myristoylation and calcium-binding. Plant Cell 12, 1667-1677.

Jaglo-Ottosen, K. R., Gilmour, S. J., Zarka, D. G., Schabenberger, O., and Thomashow, M. F. (1998). *Arabidopsis* CBF1 overexpression induces COR genes and enhances freezing tolerance. Science 280, 104-106.

Knight, H., Trewavas, A. J., and Knight, M. R. (1997). Calcium signaling in *Arabidopsis thaliana* responding to drought and salinity. Plant J. 12, 1067-1078.

Kovtun, Y., Chiu, W. L., Tena, G., and Sheen, J. (2000). Functional analysis of oxidative stress-activated mitogen-activated protein kinase cascade in plants. Proc. Natl. Acad. Sci. USA 97, 2940-2945.

Liu, J., Ishitani, M., Halfter, U., Kim, C.-S., and Zhu, J.-K. (2000). The *Arabidopsis thaliana* SOS2 gene encodes a protein kinase that is required for salt tolerance. Proc. Natl. Acad. Sci. USA 97, 3730-3734.

Liu, J., and Zhu, J.-K. (1998). A calcium sensor homolog required for plant salt tolerance. Science 280, 1943-1945.

Murguia, J. R., Belles, J. M. & Serrano, R. (1995) Science 267, 232-234.

Ohta, M., Guo, Y., Halfter, U., and Zhu, J. K. (2003). A novel domain in the protein kinase SOS2 mediates interaction with the protein phosphatase 2C ABI2. Proc. Natl. Acad. Sci. USA 100, 11771-11776.

Qiu, Q. S., Guo, Y., Dietrich, M. A., Schumaker, K. S., and Zhu, J.-K. (2002). Regulation of SOS1, a plasma membrane $Na^+/H^+$ exchanger in *Arabidopsis thaliana*, by SOS2 and SOS3. Proc. Natl. Acad. Sci. USA 99, 8436-8441.

Qiu, Q. S., Guo, Y., Quintero, F. J., Pardo, J. M., Schumaker, K. S., and Zhu, J.-K. (2004). Regulation of vacuolar Na+/H+ exchange in *Arabidopsis thaliana* by the SOS pathway. J. Biol. Chem. 279, 207-215.

Qiu, Q. S., and Su, X. F. (1998). The influence of extracellular-side $Ca^{2+}$ on the activity of the plasma membrane $H^+$-ATPase from wheat roots. Aust. J. Plant Physiol. 25, 923-928.

Quintero, F. J., Ohta, M., Shi, H., Zhu, J.-K., and Pardo, J. M. (2002). Reconstitution in yeast of the *Arabidopsis* SOS signaling pathway for $Na^+$ homeostasis. Proc. Natl. Acad. Sci. USA 99, 9061-9066.

Rus, A., Yokoi, S., Sharkhuu, A., Reddy, M., Lee, B. H., Matsumoto, T. K., Koiwa, H., Zhu, J. K., Bressan, R. A., and Hasegawa, P. M. (2001). AtHKT1 is a salt tolerance determinant that controls Na(+) entry into plant roots. Proc. Natl. Acad. Sci. USA 98, 14150-14155.

Shi, H., Lee, B., Wu, S.-J., and Zhu, J.-K. (2003). Overexpression of a plasma membrane $Na^+/H^+$ antiporter improves salt tolerance in *Arabidopsis*. Nature Biotechnol. 21, 81-85.

Wu, S. U., Ding, L. & Zhu, J. K. (1996) Plant Cell 8, 617-627.

Zhang, H. X., and Blumwald, E. (2001). Transgenic salt-tolerant tomato plants accumulate salt in foliage but not in fruit. Nature Biotechnol. 19, 765-768.

Zhang, H. X., Hodson, J. N., Williams, J. P., and Blumwald, E. (2001). Engineering salt-tolerant *Brassica* plants: Characterization of yield and seed oil quality in transgenic plants with increased vacuolar sodium accumulation. Proc. Natl. Acad. Sci. USA 98, 12832-12836.

Zhu, J.-K. (2000). Cell signaling under salt, water and cold stresses. Curr. Opin. Plant Biol. 4, 401-406.

Zhu, J.-K. (2002). Salt and drought stress signal transduction in plants. Annu. Rev. Plant Biol. 53, 247-273.

Zhu, J.-K., Xiong, L., Ishitani, M., Liu, J., Lee, H., Stevenson, B., and Shi, W. (1998). Identification of genes important for environmental stress tolerance in plants. In Breeding and Biotechnology of Environmental Stress in Rice, Y. Sato, ed (Sapporo, Japan: Hokkaido National Agricultural Experiment Station), pp. 105-113.

---

What we claim is:

1. A method of increasing salt tolerance in a plant in need thereof, comprising overexpressing a gene encoding a mutant SOS2 protein in at least one cell type in said plant by transforming said cells with an expression cassette comprising a promoter that is functional in a plant cell operably linked to an isolated nucleic acid encoding the mutant SOS2 protein, wherein said promoter regulates overexpression and wherein said mutant SOS2 protein has the sequence of SEQ ID NO: 4.

2. The method of claim 1, wherein said mutant SOS2 protein has serine/threonine kinase activity.

3. The method of claim 1, wherein the plant is *Arabidopsis thalania*.

4. The method of claim 1, wherein the plant is selected from the group consisting of wheat, corn, peanut cotton, oat, and soybean.

5. The method of claim 1, wherein the cells in said plant overexpressing said gene are transformed with a vector containing a polynucleotide sequence that is at least 95% homologous to SEQ ID NO: 11, wherein said polynucleotide sequence encodes a protein having SOS3 calcium-binding activity.

6. The method of claim 5 wherein said polynucleotide sequence is SEQ DNO: 11.

7. The method of claim 5 wherein said polynucleotide sequence encodes the protein of SEQ ID NO: 12.

8. The method of claim 1, wherein the promoter is selected from the group consisting of a viral coat protein promoter, a tissue-specific promoter, a monocot promoter, a ubiquitin promoter, a stress inducible promoter, a CaMV 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Piac promoter, a root-cell promoter, an ABA-inducible promoter and a turgor-inducible promoter.

9. The method of claim 1, wherein said expression cassette is contained in an expression vector.

10. The method of claim 9, wherein said expression vector further comprises a polynucleotide sequence that is at least 95% homologous to SEQ ID NO: 11, wherein said polynucleotide sequence encodes a protein having SOS3 calcium-binding activity.

11. The method of claim 10 wherein said polynucleotide sequence is SEQ ID NO: 11.

12. The method of claim 10 wherein said polynucleotide sequence encodes the protein of SEQ ID NO: 12.

13. The method of claim 1, wherein said overexpressing comprises inducing expression of said gene by subjecting said plant for a sufficient time and under conditions suitable to impart salt tolerance to said plant.

14. A transgenic plant comprising a vector for expressing a gene encoding a mutant SOS2 protein in at least one cell type in said plant, wherein said mutant SOS2 protein has the sequence of SEQ ID NO: 4.

15. The transgenic plant of claim 14 wherein said vector further comprises a promoter that is functional in a plant cell operably linked to a nucleic acid encoding said mutant SOS2 protein, wherein said promoter regulates expression of said gene.

16. The transgenic plant of claim 15 wherein the promoter is selected from the group consisting of a viral coat protein promoter, a tissue-specific promoter, a monocot promoter, a ubiquitin promoter, a stress inducible promoter, a CaMV 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Ptac promoter, a root-cell promoter, an ABA-inducible promoter and a turgor-inducible promoter.

17. The transgenic plant of claim 14 further comprising an expression vector comprising a polynucleotide sequence that is at least 95% homologous to SEQ ID NO: 11, wherein said polynucleotide sequence encodes a protein having SOS3 calcium-binding activity and wherein expression of said polynucleotide sequence is controlled by a promoter that is functional in a plant cell operably linked to said polynucleotide sequence.

18. The transgenic plant of claim 17 wherein said polynucleotide sequence is SEQ ID NO: 11.

19. The transgenic plant of claim 17 wherein said polynucleotide sequence encodes the protein of SEQ ID NO: 12.

20. The transgenic plant of claim 14 wherein said plant is selected from the group consisting of wheat, corn, peanut cotton, oat, and soybean plant.

21. A method of increasing salt tolerance in a plant in need thereof, comprising overexpressing a gene encoding a mutant SOS2 protein in at least one cell type in said plant by transforming said cells with an expression cassette comprising a promoter that is functional in a plant cell operably linked to an isolated nucleic acid encoding the mutant SOS2 protein, wherein said promoter regulates overexpression and wherein said gene has the sequence of SEQ ID NO: 3.

22. The method of claim 21 wherein said gene encodes a protein having SOS2 serine/threonine kinase activity.

23. The method of claim 21 wherein the plant is *Arabidopsis thalania*.

24. The method of claim 21 wherein the plant is selected from the group consisting of wheat, corn, peanut cotton, oat, and soybean.

25. The method of claim 21 wherein the cells in said plant overexpressing said gene is transformed with a vector containing a polynucleotide sequence that is at least 95% homologous to SEQ ID NO: 11, wherein said polynucleotide sequence encodes a protein having SOS3 calcium-binding activity.

26. The method of claim 25 wherein said polynucleotide sequence is SEQ ID NO: 11.

27. The method of claim 25 wherein said polynucleotide sequence encodes the protein of SEQ ID NO: 12.

28. The method of claim 21, wherein the promoter is selected from the group consisting of a viral coat protein promoter, a tissue-specific promoter, a monocot promoter, a ubiquitin promoter, a stress inducible promoter, a CaMV 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Ptac promoter, a root-cell promoter, an ABA-inducible promoter and a turgor-inducible promoter.

29. The method of claim 21, wherein said expression cassette is contained in an expression vector.

30. The method of claim 29 wherein said expression vector further comprises a polynucleotide sequence that is at least 95% homologous to SEQ ID NO: 11, wherein said polynucleotide sequence encodes a protein having SOS3 calcium-binding activity.

31. The method of claim 30 wherein said polynucleotide sequence is SEQ ID NO: 11.

32. The method of claim 30 wherein said polynucleotide sequence encodes the protein of SEQ ID NO: 12.

33. The method of claim 21 wherein said overexpressing comprises inducing expression of said gene by subjecting said plant for a sufficient time and under conditions suitable to impart salt tolerance to said plant.

34. A transgenic plant harboring a vector for expressing a gene encoding a mutant SOS2 protein in at least one cell type in said plant, wherein said gene has the sequence group of SEQ ID NO: 3.

35. The transgenic plant of claim 34 wherein said vector further comprises a promoter that is functional in a plant cell operably linked to a nucleic acid encoding said mutant SOS2 protein, wherein said promoter regulates expression of said gene.

36. The transgenic plant of claim 35 wherein the promoter is selected from the group consisting of a viral coat protein promoter, a tissue-specific promoter, a monocot promoter, a ubiquitin promoter, a stress inducible promoter, a CaMY 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Ptac promoter, a root-cell promoter, an ABA-inducible promoter and a turgor-inducible promoter.

37. The transgenic plant of claim 34 further comprising an expression vector comprising a polynucleotide sequence that is at least 95% homologous to SEQ ID NO: 11, wherein said polynucleotide sequence encodes a protein having SOS3 calcium-binding activity and wherein expression of said polynucleotide sequence is controlled by a promoter that is functional in a plant cell operably linked to said polynucleotide sequence.

38. The transgenic plant of claim 37 wherein said polynucleotide sequence is SEQ ID NO: 11.

39. The transgenic plant of claim 37 wherein said polynucleotide sequence encodes the protein of SEQ ID NO: 12.

40. The transgenic plant of claim 34 wherein said plant is selected from the group consisting of wheat, corn, peanut cotton, oat, and soybean plant.

* * * * *

UNITED STATES PATENT AND TRADEMARK OFFICE
CERTIFICATE OF CORRECTION

PATENT NO. : 7,265,266 B2
APPLICATION NO. : 11/040005
DATED : September 4, 2007
INVENTOR(S) : Jian-Kang Zhu et al.

It is certified that error appears in the above-identified patent and that said Letters Patent is hereby corrected as shown below:

Column 3, line 48, "wheat, corn, peanut cotton, oat, or"
    should read -- wheat, corn, peanut, cotton, oat, or --.

Column 6, line 24, "25S rRNA (Ethidium bromide stained)"
    should read -- 25S rRNA (ethidium bromide stained) --;
line 48, "medium transcript levels (F) are shown."
    should read -- medium transcript +100 mM NaCl for 2 weeks (mean ± SE of three replicate experiments). *T/DSOS2DF* transcript levels (F) are shown. --.

Column 8, line 24, "acid and stress signaling (Ohta et al., 2003."
    should read -- acid and stress signaling (Ohta et al., 2003). --;
line 57, "In 10 this"
    should read -- In this --.

Column 11, line 17, "and an protein sequence of SEQ ID NO: 12."
    should read -- and a protein sequence of SEQ ID NO: 12. --.

Column 13, line 5, "where M nucleotides in the DNA,"
    should read --where M is the molarity of monovalent cations, %GC is the percentage of guanosine and cytosine nucleotides in the DNA, --.

Column 14, line 13, "wheat, corn, peanut cotton, oat,"
    should read -- wheat, corn, peanut, cotton, oat, --.

Column 20, line 37, "SOS2 May be Lmiting for"
    should read -- SOS2 May be Limiting for --.

Column 45, line 37, "wheat, corn, peanut cotton, oat,"
    should read -- wheat, corn, peanut, cotton, oat, --.

Column 45, line 47, "sequence is SEQ DNO: 11."
    should read -- sequence is SEQ ID NO: 11. --;
line 61, "a Piac promoter,"
    should read -- a Ptac promoter, --.

UNITED STATES PATENT AND TRADEMARK OFFICE
CERTIFICATE OF CORRECTION

PATENT NO. : 7,265,266 B2
APPLICATION NO. : 11/040005
DATED : September 4, 2007
INVENTOR(S) : Jian-Kang Zhu et al.

It is certified that error appears in the above-identified patent and that said Letters Patent is hereby corrected as shown below:

Column 47, lines 2-3, "wheat, corn, peanut cotton, oat,"
    should read -- wheat, corn, peanut, cotton, oat, --;
line 17, "wheat, corn, peanut cotton, oat,"
    should read -- wheat, corn, peanut, cotton, oat, --.

Column 48, line 21, "a stress inducible promoter, a CaMY"
    should read -- a stress inducible promoter, a CaMV --;
lines 45-56, "wheat, corn, peanut cotton, oat,"
    should read -- wheat, corn, peanut, cotton, oat, --.

Signed and Sealed this

Twentieth Day of May, 2008

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 1341
<212> TYPE: DNA
<213> ORGANISM: Arabidopsis thaliana

<400> SEQUENCE: 1
atgacaaaga aaatgagaag agtgggcaag tacgaggttg gtcgcacaat aggtgaagga     60
acctttgcta aggttaagtt tgcgaggaac acagacactg tgataatgt agccatcaaa     120 attatggcta agagtacaat acttaagaac agaatggttg atcagataaa aagagagata    180
tctataatga agattgttcg tcacccgaac atagtgaggt tgtatgaggt gttggcgagt    240
ccttcgaaaa tatatatagt tttggagttt gtgacaggag gagagctctt tgatagaatt    300
gttcataaag ggaggcttga agaaagtgag tctcggaaat actttcaaca gcttgtagat    360
gctgttgctc attgtcactg caagggtgtt taccaccgtg acctaaagcc agaaaatctt    420
ttactcgata caaatggaaa tctgaaggtt tcggatttcg gactcagtgc attgcctcag    480
```

```
gaaggagtag aacttctgcg taccacatgt ggaactccga actatgtagc tccagaggta      540
cttagtggac agggttacga tggttcagca gctgatattt ggtcttgcgg ggttattctt      600
ttcgttatat tggctggata tttacctttt tccgagacgg atcttccagg gttgtacaga      660
aaaataaatg cagcagagtt ttcttgtcca ccgtggtttt ccgcagaagt gaagttttta      720
atacatagga tacttgaccc caatcccaaa acacgtattc aaattcaagg aatcaagaaa      780
gatccttggt tcagattaaa ttatgtgcct atacgagcaa gggaagaaga agaagtgaat      840
ttggatgata ttcgtgcagt ttttgatgga attgagggca gttatgtagc ggagaatgta      900
gagagaaatg atgaagggcc cctgatgatg aatgcctttg agatgattac cttatcacaa      960
ggcttaaatt tatctgcact atttgacagg cgacaggatt ttgttaaaag gcaaacccgt     1020
tttgtttctc gaagggaacc tagtgagata attgctaaca ttgaggctgt agcgaactca     1080
atgggtttta agtctcatac acgaaacttc aagacaaggc tcgagggatt atcttcgatc     1140
aaggccggac agttagctgt tgtgatagag atttacgagg tggcaccatc gcttttcatg     1200
gtagacgtaa gaaaggctgc tggtgaaact cttgaatatc acaagttcta caagaagcta     1260
tgttcgaaac tggaaaacat aatatggagg gcaacagaag gaataccaaa gtcagagatt     1320
ctcagaacaa tcacgttttg a                                               1341
```

<210> SEQ ID NO 2
<211> LENGTH: 446
<212> TYPE: PRT
<213> ORGANISM: Arabidopsis thaliana

<400> SEQUENCE: 2

```
Met Thr Lys Lys Met Arg Arg Val Gly Lys Tyr Glu Val Gly Arg Thr
  1               5                  10                  15

Ile Gly Glu Gly Thr Phe Ala Lys Val Lys Phe Ala Arg Asn Thr Asp
                 20                  25                  30

Thr Gly Asp Asn Val Ala Ile Lys Ile Met Ala Lys Ser Thr Ile Leu
             35                  40                  45

Lys Asn Arg Met Val Asp Gln Ile Lys Arg Glu Ile Ser Ile Met Lys
 50                  55                  60

Ile Val Arg His Pro Asn Ile Val Arg Leu Tyr Glu Val Leu Ala Ser
 65                  70                  75                  80

Pro Ser Lys Ile Tyr Ile Val Leu Glu Phe Val Thr Gly Gly Glu Leu
                 85                  90                  95

Phe Asp Arg Ile Val His Lys Gly Arg Leu Glu Glu Ser Glu Ser Arg
            100                 105                 110

Lys Tyr Phe Gln Gln Leu Val Asp Ala Val Ala His Cys His Cys Lys
        115                 120                 125

Gly Val Tyr His Arg Asp Leu Lys Pro Glu Asn Leu Leu Leu Asp Thr
    130                 135                 140

Asn Gly Asn Leu Lys Val Ser Asp Phe Gly Leu Ser Ala Leu Pro Gln
145                 150                 155                 160

Glu Gly Val Glu Leu Leu Arg Thr Thr Cys Gly Thr Pro Asn Tyr Val
                165                 170                 175

Ala Pro Glu Val Leu Ser Gly Gln Gly Tyr Asp Gly Ser Ala Ala Asp
            180                 185                 190

Ile Trp Ser Cys Gly Val Ile Leu Phe Val Ile Leu Ala Gly Tyr Leu
        195                 200                 205

Pro Phe Ser Glu Thr Asp Leu Pro Gly Leu Tyr Arg Lys Ile Asn Ala
    210                 215                 220
```

```
Ala Glu Phe Ser Cys Pro Pro Trp Phe Ser Ala Glu Val Lys Phe Leu
225                 230                 235                 240

Ile His Arg Ile Leu Asp Pro Asn Pro Lys Thr Arg Ile Gln Ile Gln
            245                 250                 255

Gly Ile Lys Lys Asp Pro Trp Phe Arg Leu Asn Tyr Val Pro Ile Arg
        260                 265                 270

Ala Arg Glu Glu Glu Val Asn Leu Asp Asp Ile Arg Ala Val Phe
    275                 280                 285

Asp Gly Ile Glu Gly Ser Tyr Val Ala Glu Asn Val Glu Arg Asn Asp
        290                 295                 300

Glu Gly Pro Leu Met Met Asn Ala Phe Glu Met Ile Thr Leu Ser Gln
305                 310                 315                 320

Gly Leu Asn Leu Ser Ala Leu Phe Asp Arg Arg Gln Asp Phe Val Lys
                325                 330                 335

Arg Gln Thr Arg Phe Val Ser Arg Arg Glu Pro Ser Glu Ile Ile Ala
            340                 345                 350

Asn Ile Glu Ala Val Ala Asn Ser Met Gly Phe Lys Ser His Thr Arg
        355                 360                 365

Asn Phe Lys Thr Arg Leu Glu Gly Leu Ser Ser Ile Lys Ala Gly Gln
    370                 375                 380

Leu Ala Val Val Ile Glu Ile Tyr Glu Val Ala Pro Ser Leu Phe Met
385                 390                 395                 400

Val Asp Val Arg Lys Ala Ala Gly Glu Thr Leu Glu Tyr His Lys Phe
                405                 410                 415

Tyr Lys Lys Leu Cys Ser Lys Leu Glu Asn Ile Ile Trp Arg Ala Thr
            420                 425                 430

Glu Gly Ile Pro Lys Ser Glu Ile Leu Arg Thr Ile Thr Phe
        435                 440                 445

<210> SEQ ID NO 3
<211> LENGTH: 1341
<212> TYPE: DNA
<213> ORGANISM: Artificial Sequence
<220> FEATURE:
<223> OTHER INFORMATION: Synthetic DNA

<400> SEQUENCE: 3
atgacaaaga aaatgagaag agtgggcaag tacgaggttg gtcgcacaat aggtgaagga      60
acctttgcta aggttaagtt tgcgaggaac acagacactg gtgataatgt agccatcaaa    120
attatggcta agagtacaat acttaagaac agaatggttg atcagataaa agagagata    180 tctataatga agattgttcg tcacccgaac atagtgaggt tgtatgaggt gttggcgagt    240
ccttcgaaaa tatatatagt tttggagttt gtgacaggag agagctctt tgatagaatt    300 gttcataaag ggaggcttga agaaagtgag tctcggaaat actttcaaca gcttgtagat    360
gctgttgctc attgtcactg caagggtgtt taccaccgtg acctaaagcc agaaaatctt    420
ttactcgata caaatggaaa tctgaaggtt tcggatttcg gactcagtgc attgcctcag    480
gaaggagtag aacttctgcg tgacacatgt ggaactccga actatgtagc tccagaggta    540
cttagtggac agggttacga tggttcagca gctgatattt ggtcttgcgg ggttattctt    600
ttcgttatat tggctggata tttacctttt tccgagacgg atcttccagg ttgtacaga    660 aaaataaatg cagcagagtt ttcttgtcca ccgtggtttt ccgcagaagt gaagttttta    720
atacatagga tacttgaccc caatcccaaa acacgtattc aaattcaagg aatcaagaaa    780
```

-continued

```
gatccttggt tcagattaaa ttatgtgcct atacgagcaa gggaagaaga agaagtgaat    840
ttggatgata ttcgtgcagt ttttgatgga attgagggca gttatgtagc ggagaatgta    900
gagagaaatg atgaagggcc cctgatgatg aatgcctttg agatgattac cttatcacaa    960
ggcttaaatt tatctgcact atttgacagg cgacaggatt ttgttaaaag gcaaacccgt   1020
tttgtttctc gaagggaacc tagtgagata attgctaaca ttgaggctgt agcgaactca   1080
atgggtttta agtctcatac acgaaacttc aagacaaggc tcgagggatt atcttcgatc   1140
aaggccggac agttagctgt tgtgatagag atttacgagg tggcaccatc gcttttcatg   1200
gtagacgtaa gaaaggctgc tggtgaaact cttgaatatc acaagttcta caagaagcta   1260
tgttcgaaac tggaaaacat aatatggagg gcaacagaag gaataccaaa gtcagagatt   1320
ctcagaacaa tcacgttttg a                                             1341
```

<210> SEQ ID NO 4
<211> LENGTH: 446
<212> TYPE: PRT
<213> ORGANISM: Artificial Sequence
<220> FEATURE:
<223> OTHER INFORMATION: Synthetic Polypeptide

<400> SEQUENCE: 4

```
Met Thr Lys Lys Met Arg Arg Val Gly Lys Tyr Glu Val Gly Arg Thr
1               5                   10                  15

Ile Gly Glu Gly Thr Phe Ala Lys Val Lys Phe Ala Arg Asn Thr Asp
            20                  25                  30

Thr Gly Asp Asn Val Ala Ile Lys Ile Met Ala Lys Ser Thr Ile Leu
        35                  40                  45

Lys Asn Arg Met Val Asp Gln Ile Lys Arg Glu Ile Ser Ile Met Lys
    50                  55                  60

Ile Val Arg His Pro Asn Ile Val Arg Leu Tyr Glu Val Leu Ala Ser
65                  70                  75                  80

Pro Ser Lys Ile Tyr Ile Val Leu Glu Phe Val Thr Gly Gly Glu Leu
                85                  90                  95

Phe Asp Arg Ile Val His Lys Gly Arg Leu Glu Glu Ser Glu Ser Arg
            100                 105                 110

Lys Tyr Phe Gln Gln Leu Val Asp Ala Val Ala His Cys His Cys Lys
        115                 120                 125

Gly Val Tyr His Arg Asp Leu Lys Pro Glu Asn Leu Leu Leu Asp Thr
    130                 135                 140

Asn Gly Asn Leu Lys Val Ser Asp Phe Gly Leu Ser Ala Leu Pro Gln
145                 150                 155                 160

Glu Gly Val Glu Leu Leu Arg Asp Thr Cys Gly Thr Pro Asn Tyr Val
                165                 170                 175

Ala Pro Glu Val Leu Ser Gly Gln Gly Tyr Asp Gly Ser Ala Ala Asp
            180                 185                 190

Ile Trp Ser Cys Gly Val Ile Leu Phe Val Ile Leu Ala Gly Tyr Leu
        195                 200                 205

Pro Phe Ser Glu Thr Asp Leu Pro Gly Leu Tyr Arg Lys Ile Asn Ala
    210                 215                 220

Ala Glu Phe Ser Cys Pro Pro Trp Phe Ser Ala Glu Val Lys Phe Leu
225                 230                 235                 240

Ile His Arg Ile Leu Asp Pro Asn Pro Lys Thr Arg Ile Gln Ile Gln
                245                 250                 255

Gly Ile Lys Lys Asp Pro Trp Phe Arg Leu Asn Tyr Val Pro Ile Arg
```

```
                260               265               270
Ala Arg Glu Glu Glu Val Asn Leu Asp Asp Ile Arg Ala Val Phe
            275               280               285
Asp Gly Ile Glu Gly Ser Tyr Val Ala Glu Asn Val Glu Arg Asn Asp
        290               295               300
Glu Gly Pro Leu Met Met Asn Ala Phe Glu Met Ile Thr Leu Ser Gln
305               310               315               320
Gly Leu Asn Leu Ser Ala Leu Phe Asp Arg Arg Gln Asp Phe Val Lys
                325               330               335
Arg Gln Thr Arg Phe Val Ser Arg Arg Glu Pro Ser Glu Ile Ile Ala
            340               345               350
Asn Ile Glu Ala Val Ala Asn Ser Met Gly Phe Lys Ser His Thr Arg
            355               360               365
Asn Phe Lys Thr Arg Leu Glu Gly Leu Ser Ser Ile Lys Ala Gly Gln
            370               375               380
Leu Ala Val Val Ile Glu Ile Tyr Glu Val Ala Pro Ser Leu Phe Met
385               390               395               400
Val Asp Val Arg Lys Ala Ala Gly Glu Thr Leu Glu Tyr His Lys Phe
                405               410               415
Tyr Lys Lys Leu Cys Ser Lys Leu Glu Asn Ile Ile Trp Arg Ala Thr
            420               425               430
Glu Gly Ile Pro Lys Ser Glu Ile Leu Arg Thr Ile Thr Phe
            435               440               445

<210> SEQ ID NO 5
<211> LENGTH: 927
<212> TYPE: DNA
<213> ORGANISM: Artificial Sequence
<220> FEATURE:
<223> OTHER INFORMATION: Synthetic DNA

<400> SEQUENCE: 5
atgacaaaga aaatgagaag agtgggcaag tacgaggttg gtcgcacaat aggtgaagga      60
acctttgcta aggttaagtt tgcgaggaac acagacactg tgataatgt agccatcaaa     120 attatggcta agagtacaat acttaagaac agaatggttg atcagataaa aagagagata     180
tctataatga agattgttcg tcacccgaac atagtgaggt tgtatgaggt gttggcgagt     240
ccttcgaaaa tatatatagt tttggagttt gtgacaggag gagagctctt tgatagaatt     300
gttcataaag ggaggcttga agaaagtgag tctcggaaat actttcaaca gcttgtagat     360
gctgttgctc attgtcactg caagggtgtt taccaccgtg acctaaagcc agaaaatctt     420
ttactcgata caaatggaaa tctgaaggtt tcggatttcg gactcagtgc attgcctcag     480
gaaggagtag aacttctgcg tgacacatgt ggaactccga actatgtagc tccagaggta     540
cttagtggac agggttacga tggttcagca gctgatattt ggtcttgcgg ggttattctt     600
ttcgttatat tggctggata tttacctttt tccgagacgg atcttccagg gttgtacaga     660
aaaataaatg cagcagagtt ttcttgtcca ccgtggtttt ccgcagaagt gaagttttta     720
atacatagga tacttgaccc caatcccaaa acacgtattc aaattcaagg aatcaagaaa     780
gatccttggt tcagattaaa ttatgtgcct atacgagcaa gggaagaaga agaagtgaat     840
ttggatgata ttcgtgcagt ttttgatgga attgagggca gttatgtagc ggagaatgta     900
gagagaaatg atgaagggcc cctgtga                                         927

<210> SEQ ID NO 6
```

<211> LENGTH: 308
<212> TYPE: PRT
<213> ORGANISM: Artificial Sequence
<220> FEATURE:
<223> OTHER INFORMATION: Synthetic Polypeptide

<400> SEQUENCE: 6

| | | | | | | | | | | | | | | | |
|---|---|---|---|---|---|---|---|---|---|---|---|---|---|---|---|
| Met | Thr | Lys | Lys | Met | Arg | Arg | Val | Gly | Lys | Tyr | Glu | Val | Gly | Arg | Thr |
| 1 | | | | 5 | | | | | 10 | | | | | 15 | |
| Ile | Gly | Glu | Gly | Thr | Phe | Ala | Lys | Val | Lys | Phe | Ala | Arg | Asn | Thr | Asp |
| | | | 20 | | | | | 25 | | | | | 30 | | |
| Thr | Gly | Asp | Asn | Val | Ala | Ile | Lys | Ile | Met | Ala | Lys | Ser | Thr | Ile | Leu |
| | | | 35 | | | | | 40 | | | | | 45 | | |
| Lys | Asn | Arg | Met | Val | Asp | Gln | Ile | Lys | Arg | Glu | Ile | Ser | Ile | Met | Lys |
| | 50 | | | | | 55 | | | | | 60 | | | | |
| Ile | Val | Arg | His | Pro | Asn | Ile | Val | Arg | Leu | Tyr | Glu | Val | Leu | Ala | Ser |
| 65 | | | | | 70 | | | | | 75 | | | | | 80 |
| Pro | Ser | Lys | Ile | Tyr | Ile | Val | Leu | Glu | Phe | Val | Thr | Gly | Gly | Glu | Leu |
| | | | | 85 | | | | | 90 | | | | | 95 | |
| Phe | Asp | Arg | Ile | Val | His | Lys | Gly | Arg | Leu | Glu | Glu | Ser | Glu | Ser | Arg |
| | | | 100 | | | | | 105 | | | | | 110 | | |
| Lys | Tyr | Phe | Gln | Gln | Leu | Val | Asp | Ala | Val | Ala | His | Cys | His | Cys | Lys |
| | | | 115 | | | | | 120 | | | | | 125 | | |
| Gly | Val | Tyr | His | Arg | Asp | Leu | Lys | Pro | Glu | Asn | Leu | Leu | Leu | Asp | Thr |
| | 130 | | | | | 135 | | | | | 140 | | | | |
| Asn | Gly | Asn | Leu | Lys | Val | Ser | Asp | Phe | Gly | Leu | Ser | Ala | Leu | Pro | Gln |
| 145 | | | | | 150 | | | | | 155 | | | | | 160 |
| Glu | Gly | Val | Glu | Leu | Leu | Arg | Asp | Thr | Cys | Gly | Thr | Pro | Asn | Tyr | Val |
| | | | | 165 | | | | | 170 | | | | | 175 | |
| Ala | Pro | Glu | Val | Leu | Ser | Gly | Gln | Gly | Tyr | Asp | Gly | Ser | Ala | Ala | Asp |
| | | | 180 | | | | | 185 | | | | | 190 | | |
| Ile | Trp | Ser | Cys | Gly | Val | Ile | Leu | Phe | Val | Ile | Leu | Ala | Gly | Tyr | Leu |
| | | | 195 | | | | | 200 | | | | | 205 | | |
| Pro | Phe | Ser | Glu | Thr | Asp | Leu | Pro | Gly | Leu | Tyr | Arg | Lys | Ile | Asn | Ala |
| | 210 | | | | | 215 | | | | | 220 | | | | |
| Ala | Glu | Phe | Ser | Cys | Pro | Pro | Trp | Phe | Ser | Ala | Glu | Val | Lys | Phe | Leu |
| 225 | | | | | 230 | | | | | 235 | | | | | 240 |
| Ile | His | Arg | Ile | Leu | Asp | Pro | Asn | Pro | Lys | Thr | Arg | Ile | Gln | Ile | Gln |
| | | | | 245 | | | | | 250 | | | | | 255 | |
| Gly | Ile | Lys | Lys | Asp | Pro | Trp | Phe | Arg | Leu | Asn | Tyr | Val | Pro | Ile | Arg |
| | | | 260 | | | | | 265 | | | | | 270 | | |
| Ala | Arg | Glu | Glu | Glu | Glu | Val | Asn | Leu | Asp | Asp | Ile | Arg | Ala | Val | Phe |
| | | | 275 | | | | | 280 | | | | | 285 | | |
| Asp | Gly | Ile | Glu | Gly | Ser | Tyr | Val | Ala | Glu | Asn | Val | Glu | Arg | Asn | Asp |
| | 290 | | | | | 295 | | | | | 300 | | | | |
| Glu | Gly | Pro | Leu | | | | | | | | | | | | |
| 305 | | | | | | | | | | | | | | | |

<210> SEQ ID NO 7
<211> LENGTH: 990
<212> TYPE: DNA
<213> ORGANISM: Artificial Sequence
<220> FEATURE:
<223> OTHER INFORMATION: Synthetic DNA

<400> SEQUENCE: 7
atgacaaaga aaatgagaag agtgggcaag tacgaggttg gtcgcacaat aggtgaagga    60

```
acctttgcta aggttaagtt tgcgaggaac acagacactg gtgataatgt agccatcaaa      120
attatggcta agagtacaat acttaagaac agaatggttg atcagataaa aagagagata      180
tctataatga agattgttcg tcacccgaac atagtgaggt tgtatgaggt gttggcgagt      240
ccttcgaaaa tatatatagt tttggagttt gtgacaggag gagagctctt tgatagaatt      300
gttcataaag ggaggcttga agaaagtgag tctcggaaat actttcaaca gcttgtagat      360
gctgttgctc attgtcactg caagggtgtt taccaccgtg acctaaagcc agaaaatctt      420
ttactcgata caaatggaaa tctgaaggtt tcggatttcg gactcagtgc attgcctcag      480
gaaggagtag aacttctgcg tgacacatgt ggaactccga actatgtagc tccagaggta      540
cttagtggac agggttacga tggttcagca gctgatattt ggtcttgcgg ggttattctt      600
ttcgttatat tggctggata tttacctttt tccgagacgg atcttccagg gttgtacaga      660
aaaataaatg cagcagagtt ttcttgtcca ccgtggtttt ccgcagaagt gaagttttta      720
atacatagga tacttgaccc caatcccaaa acacgtattc aaattcaagg aatcaagaaa      780
gatccttggt tcagattaaa ttatgtgcct atacgagcaa gggaagaaga agaagtgaat      840
ttggatgata ttcgtgcagt ttttgatgga attgagggca gttatgtagc ggagaatgta      900
gagagaaatg atgaagggcc cctgatgatg aatgcctttg agatgattac cttatcacaa      960
ggcttaaatt tatctgcact atttgactga                                      990
```

<210> SEQ ID NO 8
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 8

```
Met Thr Lys Lys Met Arg Arg Val Gly Lys Tyr Glu Val Gly Arg Thr
1               5                   10                  15

Ile Gly Glu Gly Thr Phe Ala Lys Val Lys Phe Ala Arg Asn Thr Asp
                20                  25                  30

Thr Gly Asp Asn Val Ala Ile Lys Ile Met Ala Lys Ser Thr Ile Leu
            35                  40                  45

Lys Asn Arg Met Val Asp Gln Ile Lys Arg Glu Ile Ser Ile Met Lys
        50                  55                  60

Ile Val Arg His Pro Asn Ile Val Arg Leu Tyr Glu Val Leu Ala Ser
65                  70                  75                  80

Pro Ser Lys Ile Tyr Ile Val Leu Glu Phe Val Thr Gly Gly Glu Leu
                85                  90                  95

Phe Asp Arg Ile Val His Lys Gly Arg Leu Glu Glu Ser Glu Ser Arg
                100                 105                 110

Lys Tyr Phe Gln Gln Leu Val Asp Ala Val Ala His Cys His Cys Lys
            115                 120                 125

Gly Val Tyr His Arg Asp Leu Lys Pro Glu Asn Leu Leu Leu Asp Thr
        130                 135                 140

Asn Gly Asn Leu Lys Val Ser Asp Phe Gly Leu Ser Ala Leu Pro Gln
145                 150                 155                 160

Glu Gly Val Glu Leu Leu Arg Asp Thr Cys Gly Thr Pro Asn Tyr Val
                165                 170                 175

Ala Pro Glu Val Leu Ser Gly Gln Gly Tyr Asp Gly Ser Ala Ala Asp
                180                 185                 190
```

```
Ile Trp Ser Cys Gly Val Ile Leu Phe Val Ile Leu Ala Gly Tyr Leu
        195                 200                 205

Pro Phe Ser Glu Thr Asp Leu Pro Gly Leu Tyr Arg Lys Ile Asn Ala
210                 215                 220

Ala Glu Phe Ser Cys Pro Pro Trp Phe Ser Ala Glu Val Lys Phe Leu
225                 230                 235                 240

Ile His Arg Ile Leu Asp Pro Asn Pro Lys Thr Arg Ile Gln Ile Gln
                245                 250                 255

Gly Ile Lys Lys Asp Pro Trp Phe Arg Leu Asn Tyr Val Pro Ile Arg
                260                 265                 270

Ala Arg Glu Glu Glu Val Asn Leu Asp Asp Ile Arg Ala Val Phe
        275                 280                 285

Asp Gly Ile Glu Gly Ser Tyr Val Ala Glu Asn Val Glu Arg Asn Asp
290                 295                 300

Glu Gly Pro Leu Met Met Asn Ala Phe Glu Met Ile Thr Leu Ser Gln
305                 310                 315                 320

Gly Leu Asn Leu Ser Ala Leu Phe Asp
                325
```

<210> SEQ ID NO 9
<211> LENGTH: 1278
<212> TYPE: DNA
<213> ORGANISM: Artificial Sequence
<220> FEATURE:
<223> OTHER INFORMATION: Synthetic DNA

<400> SEQUENCE: 9

```
atgacaaaga aaatgagaag agtgggcaag tacgaggttg gtcgcacaat aggtgaagga      60
acctttgcta aggttaagtt tgcgaggaac acagacactg tgataatgt agccatcaaa     120
attatggcta agagtacaat acttaagaac agaatggttg atcagataaa agagagata    180
tctataatga agattgttcg tcacccgaac atagtgaggt tgtatgaggt gttggcgagt    240
ccttcgaaaa tatatatagt tttggagttt gtgacaggag agagctctt tgatagaatt    300
gttcataaag ggaggcttga agaaagtgag tctcggaaat actttcaaca gcttgtagat    360
gctgttgctc attgtcactg caagggtgtt taccaccgtg acctaaagcc agaaaatctt    420
ttactcgata caaatggaaa tctgaaggtt tcggatttcg gactcagtgc attgcctcag    480
gaaggagtag aacttctgcg tgacacatgt ggaactccga actatgtagc tccagaggta    540
cttagtggac agggttacga tggttcagca gctgatattt ggtcttgcgg ggttattctt    600
ttcgttatat ggctggata tttaccttt tccgagacgg atcttccagg ttgtacaga      660
aaaataaatg cagcagagtt ttcttgtcca ccgtggtttt ccgcagaagt gaagttttta    720
atacatagga tacttgaccc caatcccaaa acacgtattc aaattcaagg aatcaagaaa    780
gatccttggt tcagattaaa ttatgtgcct atacgagcaa gggaagaaga agaagtgaat    840
ttggatgata ttcgtgcagt ttttgatgga attgagggca gttatgtagc ggagaatgta    900
gagagaaatg atgaagggcc cctgaggcga caggattttg ttaaaaggca aacccgttt    960
gtttctcgaa gggaacctag tgagataatt gctaacattg aggctgtagc gaactcaatg   1020
ggttttaagt ctcatacacg aaacttcaag acaaggctcg agggattatc ttcgatcaag   1080
gccggacagt tagctgttgt gatagagatt tacgaggtgg caccatcgct ttcatggta   1140
gacgtaagaa aggctgctgg tgaaactctt gaatatcaca gttctacaa gaagctatgt   1200
tcgaaactgg aaaacataat atggagggca acagaaggaa taccaaagtc agagattctc   1260
```
agaacaatca cgttttga                                                    1278

<210> SEQ ID NO 10
<211> LENGTH: 425
<212> TYPE: PRT
<213> ORGANISM: Artificial Sequence
<220> FEATURE:
<223> OTHER INFORMATION: Synthetic Polypeptide

<400> SEQUENCE: 10

```
Met Thr Lys Lys Met Arg Arg Val Gly Lys Tyr Glu Val Gly Arg Thr
1               5                   10                  15

Ile Gly Glu Gly Thr Phe Ala Lys Val Lys Phe Ala Arg Asn Thr Asp
            20                  25                  30

Thr Gly Asp Asn Val Ala Ile Lys Ile Met Ala Lys Ser Thr Ile Leu
        35                  40                  45

Lys Asn Arg Met Val Asp Gln Ile Lys Arg Glu Ile Ser Ile Met Lys
    50                  55                  60

Ile Val Arg His Pro Asn Ile Val Arg Leu Tyr Glu Val Leu Ala Ser
65                  70                  75                  80

Pro Ser Lys Ile Tyr Ile Val Leu Glu Phe Val Thr Gly Gly Glu Leu
                85                  90                  95

Phe Asp Arg Ile Val His Lys Gly Arg Leu Glu Glu Ser Glu Ser Arg
            100                 105                 110

Lys Tyr Phe Gln Gln Leu Val Asp Ala Val Ala His Cys His Cys Lys
        115                 120                 125

Gly Val Tyr His Arg Asp Leu Lys Pro Glu Asn Leu Leu Leu Asp Thr
    130                 135                 140

Asn Gly Asn Leu Lys Val Ser Asp Phe Gly Leu Ser Ala Leu Pro Gln
145                 150                 155                 160

Glu Gly Val Glu Leu Leu Arg Asp Thr Cys Gly Thr Pro Asn Tyr Val
                165                 170                 175

Ala Pro Glu Val Leu Ser Gly Gln Gly Tyr Asp Gly Ser Ala Ala Asp
            180                 185                 190

Ile Trp Ser Cys Gly Val Ile Leu Phe Val Ile Leu Ala Gly Tyr Leu
        195                 200                 205

Pro Phe Ser Glu Thr Asp Leu Pro Gly Leu Tyr Arg Lys Ile Asn Ala
    210                 215                 220

Ala Glu Phe Ser Cys Pro Pro Trp Phe Ser Ala Glu Val Lys Phe Leu
225                 230                 235                 240

Ile His Arg Ile Leu Asp Pro Asn Pro Lys Thr Arg Ile Gln Ile Gln
                245                 250                 255

Gly Ile Lys Lys Asp Pro Trp Phe Arg Leu Asn Tyr Val Pro Ile Arg
            260                 265                 270

Ala Arg Glu Glu Glu Val Asn Leu Asp Asp Ile Arg Ala Val Phe
        275                 280                 285

Asp Gly Ile Glu Gly Ser Tyr Val Ala Glu Asn Val Glu Arg Asn Asp
    290                 295                 300

Glu Gly Pro Leu Arg Arg Gln Asp Phe Val Lys Arg Gln Thr Arg Phe
305                 310                 315                 320

Val Ser Arg Arg Glu Pro Ser Glu Ile Ile Ala Asn Ile Glu Ala Val
                325                 330                 335

Ala Asn Ser Met Gly Phe Lys Ser His Thr Arg Asn Phe Lys Thr Arg
            340                 345                 350

Leu Glu Gly Leu Ser Ser Ile Lys Ala Gly Gln Leu Ala Val Val Ile
```

```
                355               360                365
Glu Ile Tyr Glu Val Ala Pro Ser Leu Phe Met Val Asp Val Arg Lys
        370                 375                 380

Ala Ala Gly Glu Thr Leu Glu Tyr His Lys Phe Tyr Lys Lys Leu Cys
385                 390                 395                 400

Ser Lys Leu Glu Asn Ile Ile Trp Arg Ala Thr Gly Ile Pro Lys
            405                 410                 415

Ser Glu Ile Leu Arg Thr Ile Thr Phe
            420                 425

<210> SEQ ID NO 11
<211> LENGTH: 669
<212> TYPE: DNA
<213> ORGANISM: Artificial Sequence
<220> FEATURE:
<223> OTHER INFORMATION: Synthetic DNA

<400> SEQUENCE: 11
atgggctgct ctgtatcgaa gaagaagaag aagaatgcaa tgcgaccacc gggatatgag      60
gatcccgagc ttcttgcatc cgtcacgcca ttcacggtag aagaagtgga ggctttgtat     120
gaactgttca agaagctaag cagctcaatt atcgatgatg gtcttattca taaggaagaa     180
tttcagctgg ctttattcag aataggaac cggaggaatc tcttcgctga tcggatattt      240
gatgtatttg atgtgaagcg aaatggagtg atcgagtttg gtgaatttgt ccggtcctta     300
ggtgtcttcc atccaagcgc gccggtccat gaaaaagtca aatttgcttt caagttgtac     360
gatttacgac aaactggatt catcgagcga aagaattga agagatggt agtagcgctt       420 cttcacgaat ccgaactagt tctttccgaa gatatgattg aagtaatggt ggataaggct     480
ttcgtgcaag cagaccgcaa aaacgacgga aaatcgata tagatgaatg aaagactttt     540
gtatccttga atccatcgct catcaagaac atgactttgc catatctaaa ggacataaat     600
aggacgtttc caagtttcgt ttcatcttgt gaagaggaag aaatggaatt gcaaaacgta     660
tcttcctaa                                                            669

<210> SEQ ID NO 12
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 12

Met Gly Cys Ser Val Ser Lys Lys Lys Lys Asn Ala Met Arg Pro
1               5                   10                  15

Pro Gly Tyr Glu Asp Pro Glu Leu Leu Ala Ser Val Thr Pro Phe Thr
            20                  25                  30

Val Glu Glu Val Glu Ala Leu Tyr Glu Leu Phe Lys Lys Leu Ser Ser
        35                  40                  45

Ser Ile Ile Asp Asp Gly Leu Ile His Lys Glu Glu Phe Gln Leu Ala
    50                  55                  60

Leu Phe Arg Asn Arg Asn Arg Arg Asn Leu Phe Ala Asp Arg Ile Phe
65              70                  75                  80

Asp Val Phe Asp Val Lys Arg Asn Gly Val Ile Glu Phe Gly Glu Phe
                85                  90                  95

Val Arg Ser Leu Gly Val Phe His Pro Ser Ala Pro Val His Glu Lys
            100                 105                 110
```

-continued

```
Val Lys Phe Ala Phe Lys Leu Tyr Asp Leu Arg Gln Thr Gly Phe Ile
    115                 120                 125

Glu Arg Glu Glu Leu Lys Glu Met Val Val Ala Leu Leu His Glu Ser
    130                 135                 140

Glu Leu Val Leu Ser Glu Asp Met Ile Glu Val Met Val Asp Lys Ala
145                 150                 155                 160

Phe Val Gln Ala Asp Arg Lys Asn Asp Gly Lys Ile Asp Ile Asp Glu
                165                 170                 175

Trp Lys Asp Phe Val Ser Leu Asn Pro Ser Leu Ile Lys Asn Met Thr
                180                 185                 190

Leu Pro Tyr Leu Lys Asp Ile Asn Arg Thr Phe Pro Ser Phe Val Ser
        195                 200                 205

Ser Cys Glu Glu Glu Glu Met Glu Leu Gln Asn Val Ser Ser
    210                 215                 220
```